(12) United States Patent
Nakano

(10) Patent No.: US 10,813,699 B2
(45) Date of Patent: Oct. 27, 2020

(54) MEDICAL IMAGE-PROCESSING APPARATUS, MEDICAL DIAGNOSTIC-IMAGING APPARATUS, AND MEDICAL IMAGE-PROCESSING METHOD

(71) Applicant: CANON MEDICAL SYSTEMS CORPORATION, Otawara-shi (JP)

(72) Inventor: Fumiki Nakano, Utsunomiya (JP)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 121 days.

(21) Appl. No.: 16/007,415

(22) Filed: Jun. 13, 2018

(65) Prior Publication Data
US 2018/0360542 A1  Dec. 20, 2018

(30) Foreign Application Priority Data

Jun. 14, 2017 (JP) .................... 2017-116909
May 11, 2018 (JP) .................... 2018-092400

(51) Int. Cl.
| A61B 34/10 | (2016.01) |
| A61B 6/00 | (2006.01) |
| G16H 30/20 | (2018.01) |
| G16H 30/40 | (2018.01) |
| A61M 25/00 | (2006.01) |
| G16H 20/17 | (2018.01) |

(52) U.S. Cl.
CPC .............. *A61B 34/10* (2016.02); *A61B 6/463* (2013.01); *A61B 6/487* (2013.01); *A61B 6/50* (2013.01); *A61B 6/504* (2013.01); *A61B 6/507* (2013.01); *A61B 6/5217* (2013.01); *G16H 30/20* (2018.01); *G16H 30/40* (2018.01); *A61B 2034/101* (2016.02); *A61B 2034/107* (2016.02); *A61M 25/00* (2013.01); *G16H 20/17* (2018.01)

(58) Field of Classification Search
CPC ........... A61B 6/463; A61B 6/487; A61B 6/50; A61B 6/504; A61B 6/507; A61B 6/5217; A61B 34/10; G16H 30/20; G16H 30/40
See application file for complete search history.

(56) References Cited

U.S. PATENT DOCUMENTS

2011/0282193 A1* 11/2011 Amberg ................... A61B 6/12
                                                                600/431
2014/0254906 A1   9/2014 Poole et al.

FOREIGN PATENT DOCUMENTS

JP          2014-171908          9/2014

* cited by examiner

*Primary Examiner* — Leon Flores
(74) *Attorney, Agent, or Firm* — Oblon, McClelland, Maier & Neustadt, L.L.P.

(57) ABSTRACT

A medical image-processing apparatus according to embodiments includes processing circuitry. The processing circuitry acquires volume data in which a blood vessel including a plurality of branch vessels leading to a plurality of target areas, respectively, is imaged. The processing circuitry extracts a blood vessel structure of the blood vessel included in the volume data. The processing circuitry sets a plurality of the target areas in the volume data. The processing circuitry acquires a plurality of delivery points that are points at which a drug is given to the target areas from a catheter moved inside the blood vessel based on the blood vessel structure of the blood vessel and a positional relationship between the respective target areas and the respective branch vessels in the volume data. The processing circuitry outputs the delivery points.

20 Claims, 13 Drawing Sheets

FIG.15
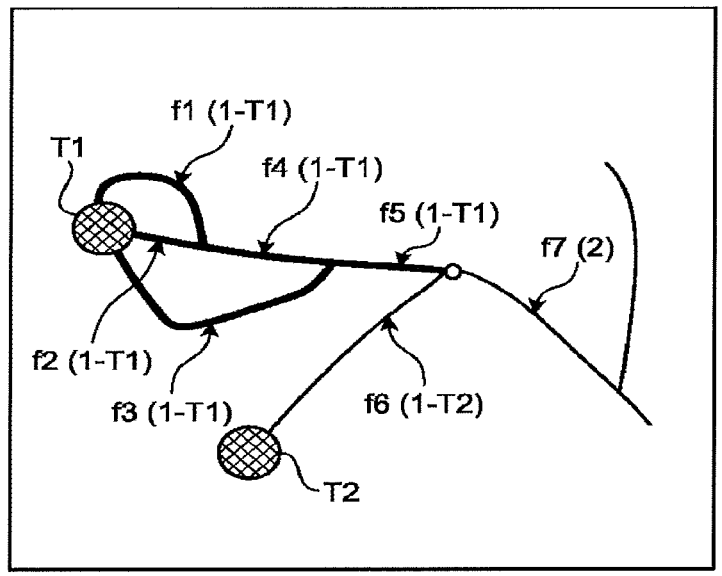
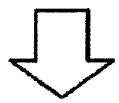
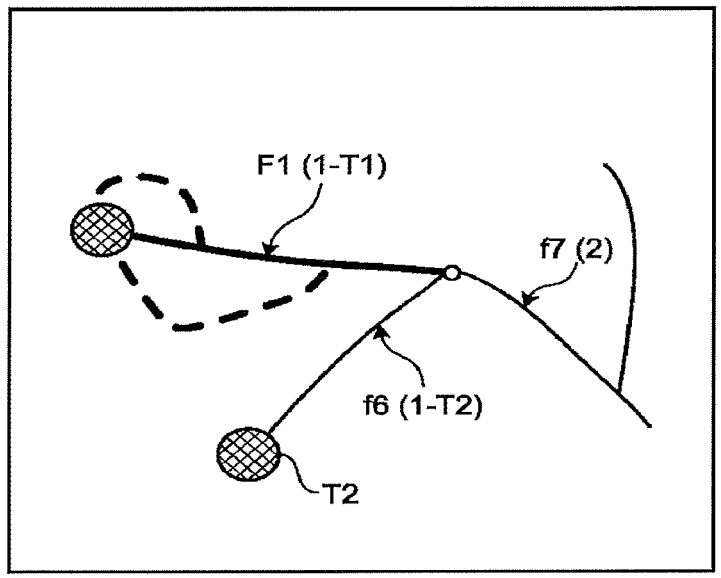

MEDICAL IMAGE-PROCESSING APPARATUS, MEDICAL DIAGNOSTIC-IMAGING APPARATUS, AND MEDICAL IMAGE-PROCESSING METHOD

CROSS-REFERENCE TO RELATED APPLICATIONS

This application is based upon and claims the benefit of priority from Japanese Patent Application No. 2017-116909, filed on Jun. 14, 2017 and Japanese Patent Application No. 2018-092400, filed on May 11, 2018; the entire contents of which are incorporated herein by reference.

FIELD

Embodiments described herein relate generally to a medical image-processing apparatus, a medical diagnostic-imaging apparatus, and a medical image-processing method.

BACKGROUND

Simulation techniques to propose a catheter moving route have conventionally been used in procedures using catheters. This simulation technique calculates a shortest route between a target area and a catheter-insertion start point, for example, from a blood vessel branching structure drawn in a contrast radiograph, and displays this as a recommended moving route. This kind of simulation technique has been used, for example, in hepatic artery embolization in which a feeding vessel is embolized to necrose a hepatic tumor.

BRIEF DESCRIPTION OF THE DRAWINGS

FIG. 15 is a diagram for explaining processing performed by an X-ray diagnostic apparatus according to a third embodiment;

DETAILED DESCRIPTION

Figure 1:
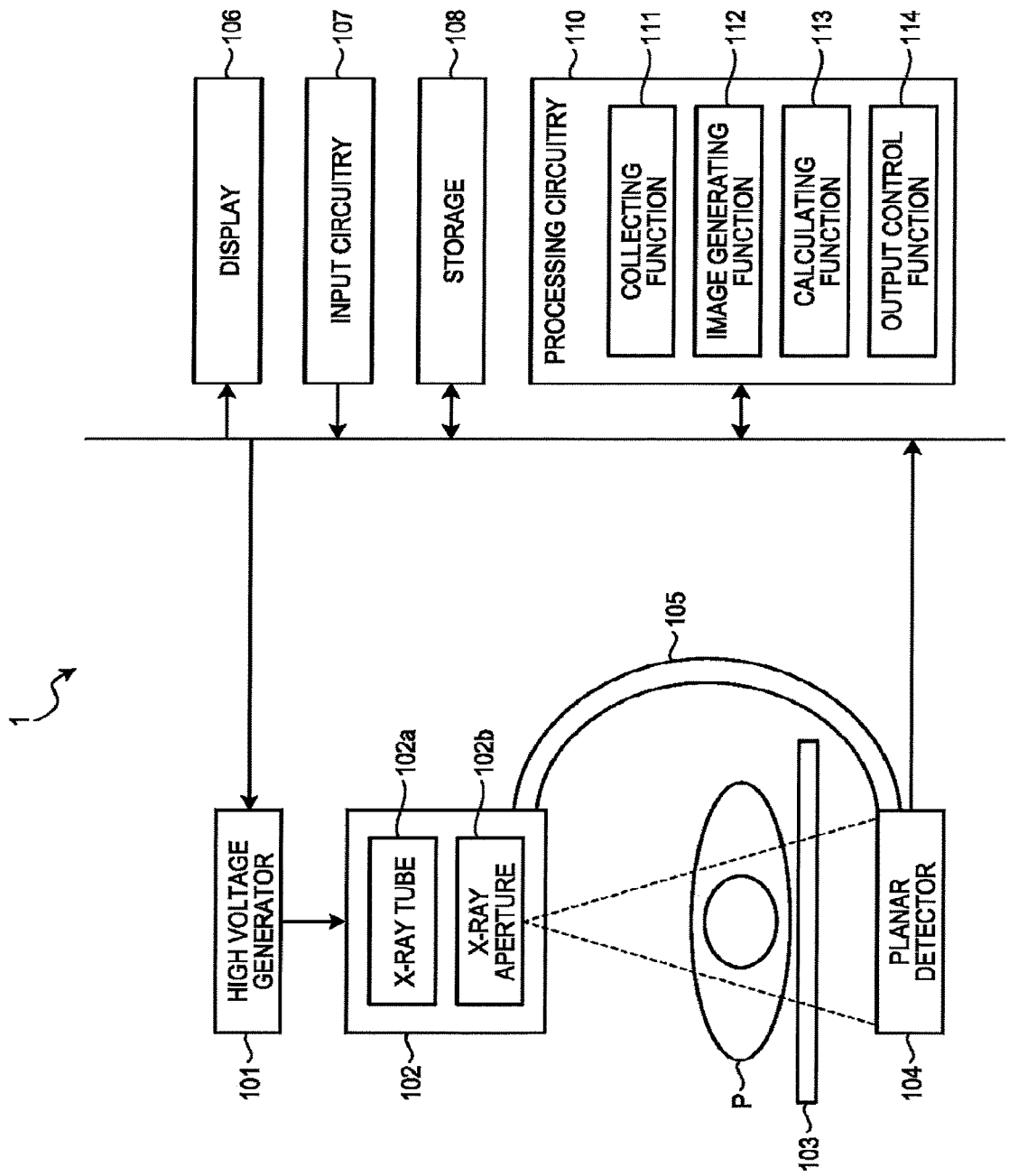
FIG. 1 is a block diagram illustrating an example of a configuration of an X-ray diagnostic apparatus according to a first embodiment.

A medical image-processing apparatus according to embodiments includes an acquiring unit, an extracting unit, a setting unit, a calculating unit, and an output control unit. The acquiring unit acquires volume data of blood vessels including branch vessels leading to respective target areas. The extracting unit extracts a blood vessel structure of the blood vessels included in the volume data. The setting unit sets plural target areas in the volume data. The calculating unit acquires plural drug delivery points at which a drug is given to the target area from a catheter moved inside the blood vessels in the volume data based on the blood vessel structure of the blood vessels and a positional relationship between the respective target areas and the respective branch vessels. The output control unit outputs the drug delivery points.

Embodiments of the medical image-processing apparatus, a medical diagnostic-imaging apparatus, and a medical image-processing method are explained in detail below referring to the drawings. The embodiments explained below are not limited to the explanation given below. Moreover, the embodiments can be combined with another embodiment or a conventional technique within a range not causing a contradiction in processing.

Application of the disclosed technique to an X-ray diagnostic apparatus is explained in the following embodiments, but embodiments are not limited thereto. For example, the disclosed technique can be applied to another medical diagnostic-imaging apparatus. As the other medical diagnostic-imaging apparatus, for example, an X-ray CT apparatus, a magnetic-resonance imaging apparatus (MRI), an ultrasonic diagnostic apparatus, a single-photon-emission computed tomography (SPECT) apparatus, a positron-emission computed tomography (PET) apparatus, a SPECT-CT apparatus in which a SPECT apparatus and a CT apparatus are integrated, a PET-CT apparatus in which a PET apparatus and an X-ray CT apparatus are integrated, or these apparatus group is applicable.

Furthermore, the disclosed technique can also be applied to a medical image-processing apparatus that has a function of processing medical images, such as a work station and a picture-archiving communication system (PACS) viewer, not limited to medical diagnostic-imaging apparatuses.

First Embodiment

First, an example of a configuration of an X-ray diagnostic apparatus 1 according to a first embodiment is explained by using FIG. 1. FIG. 1 is a block diagram illustrating an example of a configuration of the X-ray diagnostic apparatus 1 according to the first embodiment. As illustrated in FIG. 1, the X-ray diagnostic apparatus 1 according to the first embodiment includes a high voltage generator 101, an X-ray source 102, a top plate 103, a planar detector 104, a holding arm 105, a display 106, an input circuitry 107, storage 108, and processing circuitry 110.

The high voltage generator 101 is a device that generates a high voltage, for example, under control of the processing circuitry 110, and that supplies the generated high voltage to the X-ray source 102. The X-ray source 102 is a device that includes an X-ray tube 102a and an X-ray aperture 102b. The X-ray tube 102a generates X-rays by using the high voltage supplied by the high voltage generator 101. The X-ray aperture 102b controls an irradiation field for reduction of exposure of a subject P and improvement of a quality of images. The top plate 103 is, for example, a bed on which the subject P is laid, and is arranged on a table not illustrated.

The planar detector 104 is a detector that has multiple X-ray detector devices and that detects X-rays that have passed through the subject P. For example, the planar detector 104 detects distribution data indicating a signal intensity of an X-ray that has passed through the subject P, and transmits the detected distribution data to the processing circuitry 110. The holding arm 105 is a supporting member that holds the X-ray source 102 and the planar detector 104 so as to oppose to each other across the top plate 103.

The display 106 is a monitor to be viewed, for example, by an operator, and displays various kinds of X-ray images, such as an X-ray image that is collected using a contrast agent, a fluoroscopic image sequentially generated during procedures, and a mask image that is displayed superimposed on a fluoroscopic image. The mask image to be displayed is described in detail later. The input circuitry 107 includes a mouse, a keyboard, a trackball, a switch, a button, a joystick, and the like to be used to input various instructions and settings, and accepts instructions and settings from an operator.

The storage 108 is a storage device such as a memory and a hard disk drive (HDD), and stores data that is used when the processing circuitry 110 performs overall control of processing performed by the X-ray diagnostic apparatus 1. For example, the storage 108 stores various kinds of setting information that are used in X-ray image collection processing or various kinds of image processing. Moreover, the storage 108 stores various programs that are executed by the processing circuitry 110. The storage 108 stores various kinds of X-ray images.

The processing circuitry 110 is a processor that performs, for example, over all control of processing in the X-ray diagnostic apparatus 1. For example, the processing circuitry 110 performs X-ray image collection processing, various kinds of image processing, or the like as the processing in the X-ray diagnostic apparatus 1.

Furthermore, the processing circuitry 110 performs a collecting function 111, an image generating function 112, a calculating function 113, and an output control function 114. The collecting function 111 is one example of the collecting unit. The image generating function 112 is one example of an image generating unit. The calculating function 113 is one example of the calculating unit. The output control function 114 is one example of the output control unit.

The collecting function 111 controls an imaging system devices including the high voltage generator 101, the X-ray source 102, the top plate 103, the planar detector 104, and the holding arm 105, to collect X-ray projection data. Specifically, the collecting function 111 controls the imaging system devices according to various collection conditions, and thereby applies X-rays to the subject P and detects X-rays that have passed through the subject P by the planar detector 104. The collecting function 111 generates projection data using an electrical signal converted from an X-ray by the planar detector 104, and stores the generated projection data in the storage 108. For example, the collecting function 111 subjects the electrical signal received from the planar detector 104 to current-voltage conversion, analog/digital (A/D) conversion, or parallel-serial conversion, to generate projection data. The collecting function 111 is one example of the acquiring unit that acquires volume data in which blood vessels including branch vessels leading to respective target areas are imaged.

The image generating function 112 subjects the projection data stored in the storage 108 to image processing, to generate various kinds of X-ray images. For example, the image generating function 112 generates a captured image or a fluoroscopic image. Moreover, the image generating function 112 acquires differences between image data collected with a contrast agent injected to blood vessels and image data collected without injecting a contrast agent into the blood vessels, to generate a digital subtraction angiography (DSA) image. That is, the image generating function 112 can generate a blood vessel image in which the contrast agent flowing in blood vessel regions is further emphasized by removing to delete backgrounds such as bones from the blood vessel image in which the contrast agent inside the blood vessels is drawn using the contrast agent.

In the embodiment illustrated in FIG. 1, the respective processing functions performed by the collecting function 111, the image generating function 112, the calculating function 113, and the output control function 114 being components are stored in the storage 108 in a form of computer-executable program. The processing circuitry 110 is a processor that reads and executes the programs from the storage 108, thereby implementing the functions corresponding to the respective programs. In other words, the processing circuitry 110 that has read the respective programs is to have the respective functions indicated in the processing circuitry 110 in FIG. 1. Although it is explained that the processing functions performed by the collecting function 111, the image generating function 112, the calculating function 113, and the output control function 114 are implemented by a single processing circuit in FIG. 1, the processing circuit can be configured by combining multiple independent processors such that the functions are implemented by executing the programs by the respective processors. Processing performed by the calculating function 113 and the output control function 114 is described later.

The overall configuration of the X-ray diagnostic apparatus 1 according to the first embodiment has been explained in the above. With the configuration, the X-ray diagnostic apparatus 1 according to the first embodiment can present a recommended moving route of a catheter by which the catheter can move between target areas effectively.

Figure 2:
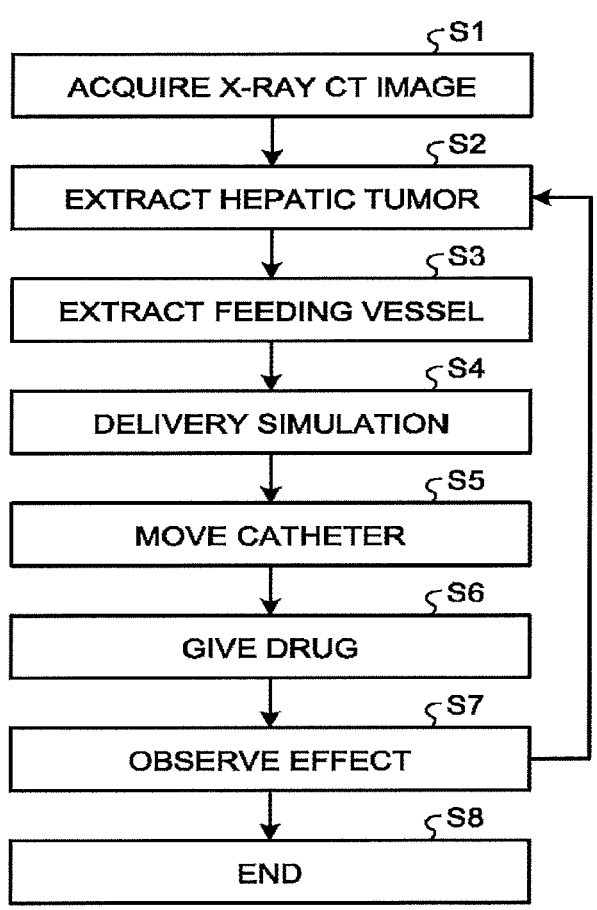
FIG. 2 is a diagram for explaining a workflow of a conventional hepatic artery embolization.

A workflow of conventional hepatic artery embolization is explained using FIG. 2. FIG. 2 is a diagram for explaining a workflow of a conventional hepatic artery embolization. The hepatic artery embolization is a procedure of causing necrosis of a hepatic tumor by embolizing a feeding vessel of the hepatic tumor. For example, a surgeon that performs the hepatic artery embolization embolizes a feeding vessel by giving a drug (blood vessel embolization agent) to embolize to the feeding vessel by using a catheter.

As illustrated in FIG. 2, in the conventional hepatic artery embolization, an X-ray CT image is first acquired (S1). Subsequently, a hepatic tumor and a feeding vessel thereof are extracted from the acquired X-ray CT image (S2, S3). Drug delivery simulation is then performed by using position information of the extracted hepatic tumor and feeding vessel (S4). In the drug delivery simulation, for example, a shortest route connecting the position of the hepatic tumor and an insertion start position of the catheter is presented as a recommended moving route.

The surgeon moves the catheter to the feeding vessel of the hepatic tumor through the recommended moving route presented (S5), and gives the drug (blood vessel embolization agent) (S6). The surgeon observes the embolization effect (S7), and ends the procedure if the feeding vessel is embolized (S8). If the feeding vessel is not embolized, the procedure is continued until the feeding vessel is embolized by moving the catheter again, or the like.

The inventors have thought that it would be useful if a recommended moving route of a catheter enabling effective movement among plural hepatic tumors can be presented in the simulation as described above. That is, it has thought that because a case with multiple hepatic tumors can be considered in the hepatic artery embolization, presenting a recommended moving route of a catheter enabling effective movement among the multiple hepatic tumors would be useful. Moreover, the inventors have thought that it would be more useful if a feeding vessel that enables to necrose some tumors at the same time can be presented.

Accordingly, the X-ray diagnostic apparatus 1 according to the first embodiment performs the respective processing functions explained below to present a recommended moving route of a catheter enabling effective movement among multiple target areas. Specifically, the collecting function 111 serving as the acquiring unit acquires volume data in which blood vessels including branch vessels leading to the respective target areas are imaged. The calculating function 113 serving as the extracting unit extracts a blood vessel structure of the blood vessels included in the volume data. The calculating function 113 serving as the setting unit sets plural target areas in the volume data. The calculating function 113 acquires plural drug delivery points at which a drug is given to a target area from the catheter moved inside the blood vessels based on the blood vessel structure of the blood vessels and a connecting state of the respective target areas and the branch vessels in the volume data, and calculates a recommended moving route of a catheter based on the drug delivery points. The output control function 114 outputs the recommended moving route.

In the present embodiment, application of the disclosed technique to the hepatic artery embolization is explained as an example, but it is not limited thereto. For example, the disclosed technique can be applied to another procedure (operation). Furthermore, in the present embodiment, a case in which a target area in the procedure using a catheter is a hepatic tumor is explained as an example, but it is not limited thereto. For example, the disclosed technique can target any area not limited to a tumor, as long as it is an area that can be a target of a procedure using a catheter.

Figure 3:
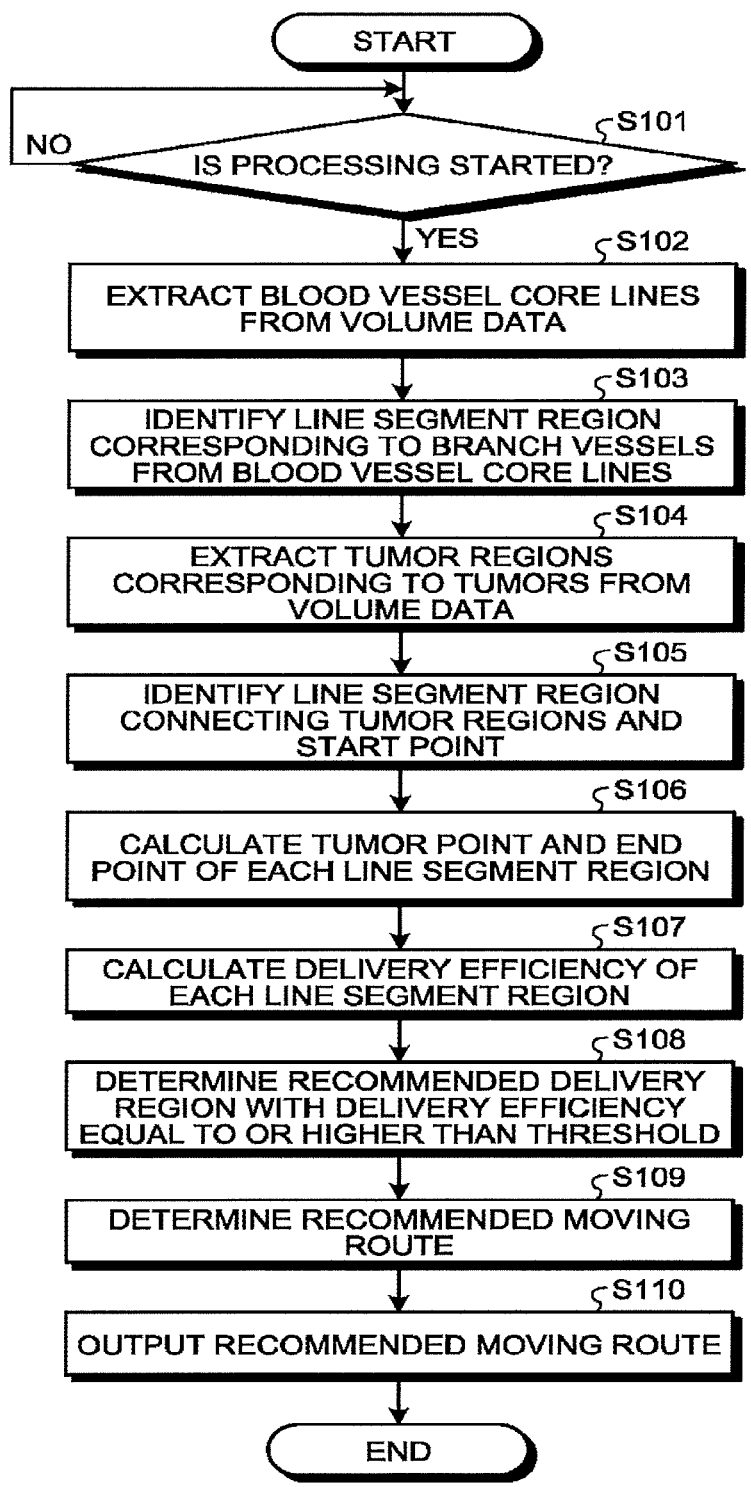
FIG. 3 is a flowchart illustrating a processing procedure of the X-ray diagnostic apparatus according to the first embodiment.

A processing procedure of the X-ray diagnostic apparatus 1 according to the first embodiment is explained using FIG. 3. FIG. 3 is a flowchart illustrating the processing procedure of the X-ray diagnostic apparatus 1 according to the first embodiment. In FIG. 3, the processing procedure of the X-ray diagnostic apparatus 1 is explained, referring to FIG. 4 to FIG. 11B. FIG. 4 to FIG. 11B are diagrams for explaining the processing performed by the X-ray diagnostic apparatus 1 according to the first embodiment. The processing procedure illustrated in FIG. 3 is started, for example, when an instruction to start simulation is input by an operator (surgeon).

In FIG. 3, a case in which a recommended moving route of a catheter is calculated, and the hepatic artery embolization is performed while displaying the calculated recommended moving route in the X-ray diagnostic apparatus 1 is explained. In this case, the surgeon can perform the procedure while viewing the recommended moving route, for example, on a monitor of the X-ray diagnostic apparatus 1. However, embodiments are not limited thereto. For example, a recommended moving route that is calculated by another medical image-processing apparatus in advance can be displayed on the monitor of the X-ray diagnostic apparatus 1.

As illustrated in FIG. 3, at step S101, the processing circuit determines whether processing has been started. For example, an operator inputs an instruction to start the simulation. When the instruction is input by the operator, the processing circuitry 110 starts processing, and performs processing at step S102 and later. When a negative determination is made at step S101, the processing circuitry 110 does not start the processing, and stays in standby state.

When a positive determination is made at step S101, the calculating function 113 extracts blood vessel core lines from volume data. The volume data is, for example, three-dimensional medical image data obtained by capturing a hepatitis of the subject P in advance. For example, the operator stores the volume data acquired in advance by the X-ray CT apparatus in the storage 108. The calculating function 113 reads the volume data from the storage 108 and performs processing.

Figure 4:
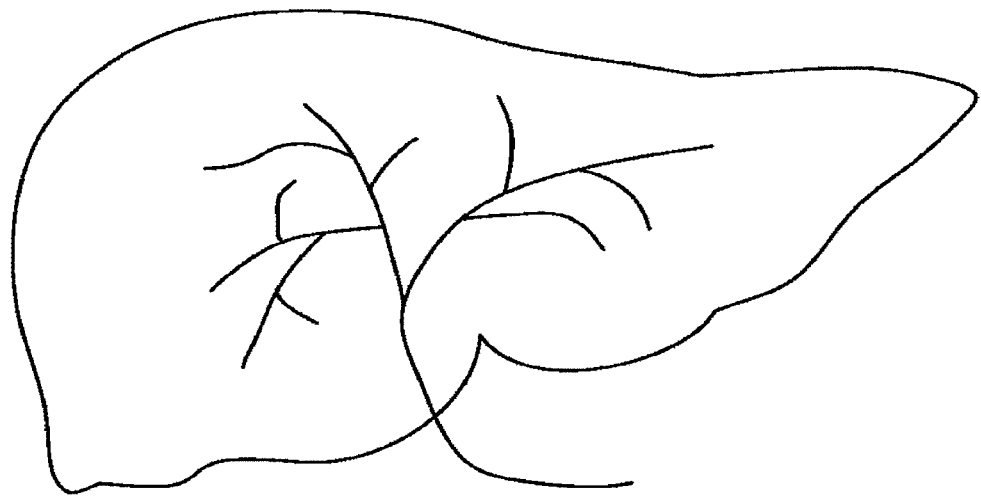
FIG. 4 is a diagram for explaining processing performed by the X-ray diagnostic apparatus according to the first embodiment.

As illustrated in FIG. 4, for example, the calculating function 113 extracts a blood vessel image of a hepatic artery from a blood vessel image drawn in the volume data. For example, the calculating function 113 extracts a blood vessel that extends from a basal portion of the hepatic artery (start point) to a tip (end) as the blood vessel image of the hepatic artery. The basal portion of the hepatic artery indicates a branch point at which hepatic arteries branches off from an abdominal aorta, and is detected, for example, by pattern matching. That is, the calculating function 113 detects a position of the basal portion of the hepatic artery by using pattern matching, and extracts a blood vessel image extending from the detected basal portion of the hepatic artery to the end as a blood vessel image of the hepatic artery. The calculating function 113 then extracts blood vessel core lines of the hepatic artery by subjecting the extracted blood vessel image of the hepatic artery to erosion. That is, the calculating function 113 serving as the extracting unit extracts a blood vessel structure of blood vessels included in the volume data.

Note that what is explained in FIG. 4 is only an example, and it is not limited thereto. For example, as a technique of extracting blood vessel core lines of a hepatic artery from volume data, any conventional technique can be applied. Moreover, a case of using a basal portion of a hepatic artery is used as the start point has been explained in FIG. 4, but it is not limited thereto. For example, the start point can be a position of an end of a catheter that is inserted into the subject P also. For example, the position of an end of a catheter can be calculated by performing positioning in advance between a fluoroscopic image acquired by the X-ray diagnostic apparatus 1 and volume data, and by detecting a projection image of a catheter from the fluoroscopic image.

The volume data is preferable to be one acquired by imaging blood vessels with a contrast agent, but it is not limited thereto, and it can be one acquired by imaging without a contrast agent. Furthermore, not limited to one acquired by an X-ray CT apparatus, the volume data can be one acquired by any medical image diagnostic apparatus such as an MRI apparatus. That is, the volume data can be any kind of image data as long as a blood vessel leading to a target area is included.

At step S103, the calculating function 113 identifies a line segment region corresponding to the branch vessels from the blood vessel core lines. The line segment region is a region corresponding to multiple line segments obtained by dividing the blood vessel core lines at branch points.

For example, the calculating function 113 detects a start point, a branch point, and an end point from the line segment region. The start point is, for example, a basal portion of a hepatic artery, and is detected by pattern matching. The branch point is a point at which the hepatic artery branches off, and is detected as a point at which one core line branches off into two or more lines. Moreover, the end point is an end portion of the hepatic artery, and is detected as a position at which a core line ends. The calculating function 113 identifies a line segment between the start point and a branch point, a line segment between a branch point and a branch point, or a line segment between a branch point and the end point as a line segment region. The calculating function 113 assigns a tag (identification information) to the identified line segment region.

Figure 5:
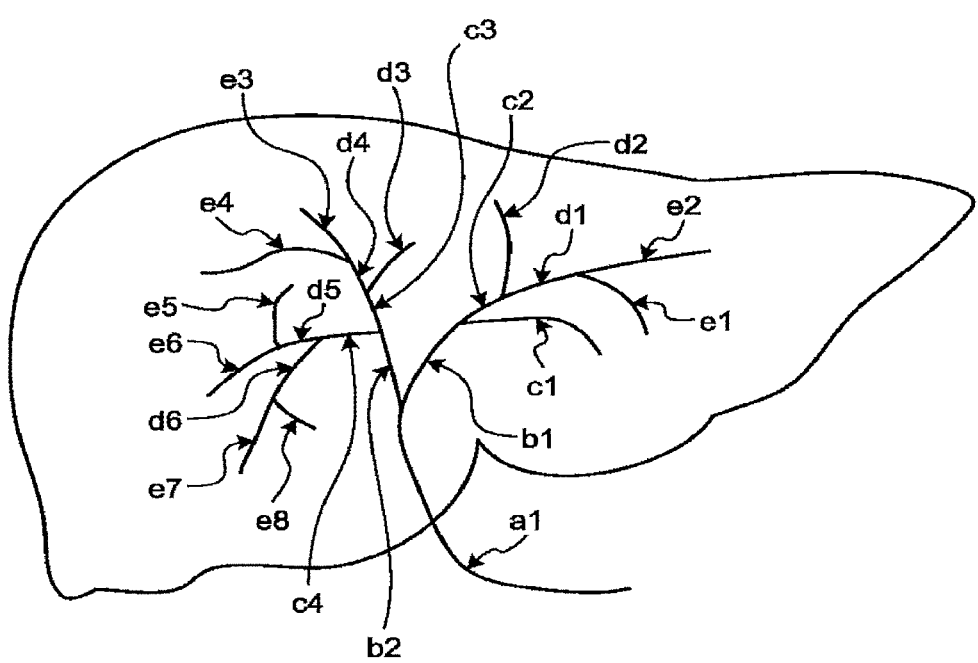
FIG. 5 is a diagram for explaining processing performed by the X-ray diagnostic apparatus according to the first embodiment.

As illustrated in FIG. 5, for example, the calculating function 113 identifies the first line segment passing the basal portion of the hepatic artery as a line segment region a1. Furthermore, the calculating function 113 identifies two line segments branching off from the line segment region a1 as a line segment region b1 and a line segment region b2. Moreover, the calculating function 113 identifies two line segments branching off from the line segment region b1 as a line segment region c1 and a line segment region c2. Furthermore, the calculating function 113 identifies two line segments branching off from the line segment region c2 as a line segment region d1 and a line segment region d2. Moreover, the calculating function 113 identifies two line segments branching off from the line segment region d1 as a line segment region e1 and a line segment region e2.

Furthermore, the calculating function 113 identifies two line segments branching off from the line segment region b1 as a line segment region c3 and a line segment region c4. Moreover, the calculating function 113 identifies two line segments branching off from the line segment region c3 as a line segment region d3 and a line segment region d4. Furthermore, the calculating function 113 identifies two line segments branching off from the line segment region d4 as a line segment region e3 and a line segment region e4.

Moreover, the calculating function 113 identifies two line segments branching off from the line segment region c4 as a line segment region d5 and a line segment region d6. Furthermore, the calculating function 113 identifies two line segments branching off from the line segment region d5 as a line segment region e5 and a line segment region e6. Moreover, the calculating function 113 identifies two line segments branching off from the line segment region d6 as a line segment region e7 and a line segment region e8.

The calculating function 113 measures length of the identified line segment regions a1, b1, b2, c1, c2, c3, c4, d1, d2, d3, d4, d5, d6, e1, e2, e3, e4, e5, e6, e7, e8. Note that what is explained in FIG. 5 is only an example, and it is not limited thereto. For example, as a technique of extracting blood vessel core lines, any conventional technique can be applied.

At step S104, the calculating function 113 extracts plural tumor regions corresponding to tumors from the volume data. For example, the calculating function 113 extracts plural tumor regions corresponding to tumors from the volume data. For example, the calculating function 113 extracts plural tumor regions from the volume data by pattern matching using features of tumors.

Figure 6:
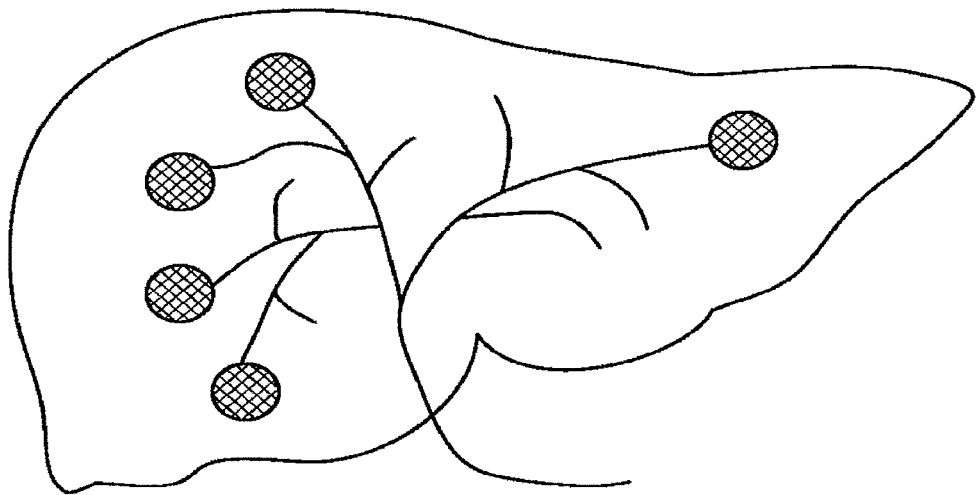
FIG. 6 is a diagram for explaining processing performed by the X-ray diagnostic apparatus according to the first embodiment.

As illustrated in FIG. 6, for example, the calculating function 113 extracts five tumor regions from the volume data. Subsequently, the calculating function 113 serving as the setting unit sets the respective extracted tumor regions as target areas.

Note that what is explained in FIG. 6 is only an example, and it is not limited thereto. For example, as a technique of extracting a tumor region, any conventional technique can be applied. Moreover, although a case in which all of the extracted tumor regions are automatically set as target areas has been explained, embodiments are not limited thereto. For example, the calculating function 113 serving as the setting unit can set arbitrary number of tumor regions specified by an operator out of the extracted five tumor regions as target areas.

At step S105, the calculating function 113 identifies a line segment region that connects the tumor regions and the start point. The start point is, for example, a basal portion of the hepatic artery. That is, the calculating function 113 identifies branch vessels being feeding vessels that supply blood to the respective tumor regions.

Figure 7:
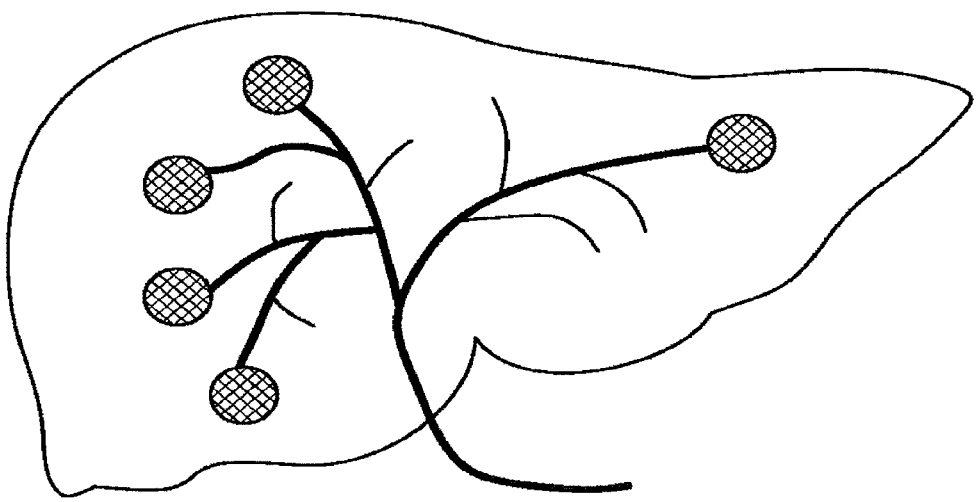
FIG. 7 is a diagram for explaining processing performed by the X-ray diagnostic apparatus according to the first embodiment.

As illustrated in FIG. 7, the calculating function 113 identifies the line segment regions a1, b1, b2, c2, c3, c4, d1, d4, d5, d6, e2, e3, e4, e6, e7 (thick lines in FIG. 7) as the feeding vessels of the five tumor regions. Specifically, the calculating function 113 identifies the line segment regions a1, b1, c2, d1, e2 as feeding vessels of a tumor region at a right end in FIG. 7. Moreover, the calculating function 113 identifies line segment regions indicating feeding vessels per tumor region, similarly for other tumor regions. Note that what is explained in FIG. 7 is only an example, and it is not limited thereto.

At step S106, the calculating function 113 calculates a tumor point and an end point of each line segment region. The tumor point expresses an evaluation value according to the number of tumors reached through the respective branch vessels. The end point expresses an evaluation value according to the number of tip portions (end portions) reached through the respective branch vessels.

Figure 8A:
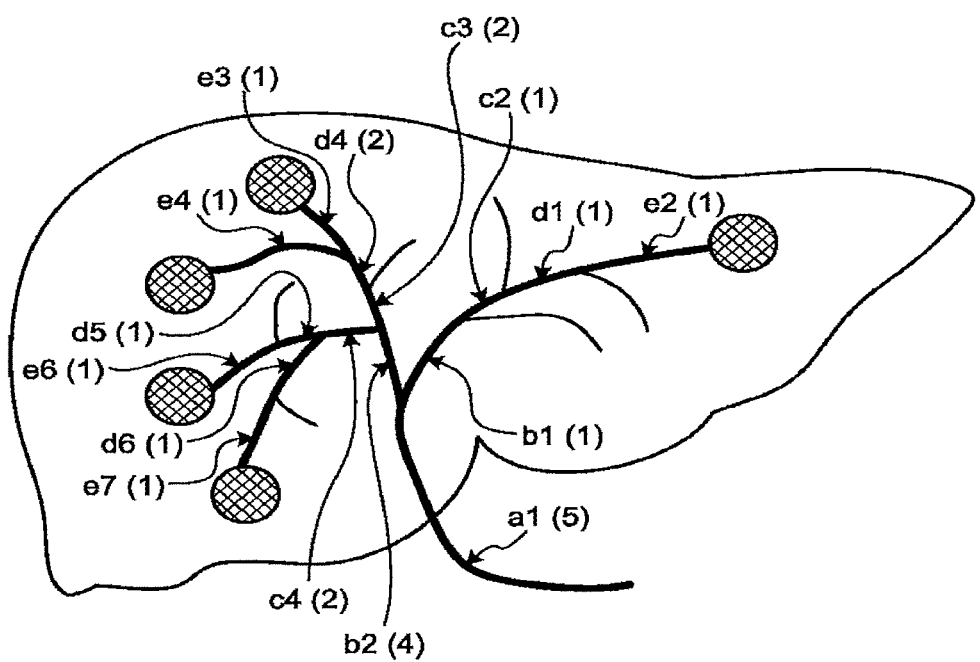
FIG. 8A and FIG. 8B are diagrams for explaining processing performed by the X-ray diagnostic apparatus according to the first embodiment.

Processing when the calculating function 113 calculates the tumor point is explained using FIG. 8A. A numeral in brackets shown beside a tag of a line segment region in FIG. 8A indicates the tumor point that is calculated for the line segment region.

As illustrated in FIG. 8A, for example, the calculating function 113 assigns a total value of tumor points of multiple branch vessels to a branch vessel at a branch source at each point at which branch vessels are unified with a branch vessel at a branch source as going upstream from ends of branch vessels.

First, the calculating function 113 calculates tumor points sequentially from a line segment region at an end. Specifically, the calculating function 113 calculates the tumor point "1" for a line segment region that is directly connected to a tumor region. That is, the calculating function 113 calculate the tumor point "1" for the five line segment regions e2, e3, e4, e6, e7 that are directly connected the tumor regions.

Next, the calculating function 113 calculates the tumor point of a line segment region at a branch source of line segment regions having the tumor point "1", going upstream from the line segment regions of the tumor point "1". For example, the calculating function 113 calculates a tumor point for the line segment region d1 that is the branch source of the line segment region e2. The line segment region d1 is a branch vessel that branches off into the line segment region e1 and the line segment region e2. To the line segment region e1, no tumor point is assigned (in other words, the tumor point is "0"), and to the line segment region e2, the tumor point "1" is assigned. In this case, the calculating function 113 calculates a total value "1" of the tumor points of the line segment region e1 and the line segment region e2, as the tumor point of the line segment region d1. This indicates that the number of tumor that is supplied with blood through the line segment region d1 is "1".

Similarly, going upstream from the line segment region d1 to the line segment region c2, the calculating function 113 calculates the tumor point "1" of the line segment region c2. Furthermore, going upstream from the line segment region c2 to the line segment region b1, the calculating function 113 calculates the tumor point "1" of the line segment region b1.

Furthermore, the calculating function 113 calculates a tumor point for the line segment region d4 that is the branch source of the line segment region e3. The line segment region d4 is a branch vessel that branches off into the line segment region e3 and the line segment region e4. To the line segment region e3 and the line segment region e4, the tumor point "1" is assigned. In this case, the calculating function 113 calculates a total value "2" of the tumor points of the line segment region e3 and the line segment region e4, as the tumor point of the line segment region d4. This indicates that the number of tumor that is supplied with blood through the line segment region d4 is "2".

Similarly, going upstream from the line segment region d4 to the line segment region c3, the calculating function 113 calculates the tumor point "2" of the line segment region c3. Moreover, the calculating function 113 calculates the tumor point "1" for the line segment regions e6, d5, e7, d6. Furthermore, the calculating function 113 calculates the tumor point "2" for the line segment region c4. Moreover, the calculating function 113 calculates the tumor point "4" for the line segment region d2. Furthermore, the calculating function 113 calculates the tumor point "5" for the line segment region a1.

As described, going upstream from a branch vessel at an end, the calculating function 113 calculates a tumor point of a branch vessel by assigning a total value of tumor points of multiple branch vessels to a branch vessel at a branch source, at each point at which multiple branch vessels are unified (merged) to a branch vessel at a branch source.

Figure 8B:
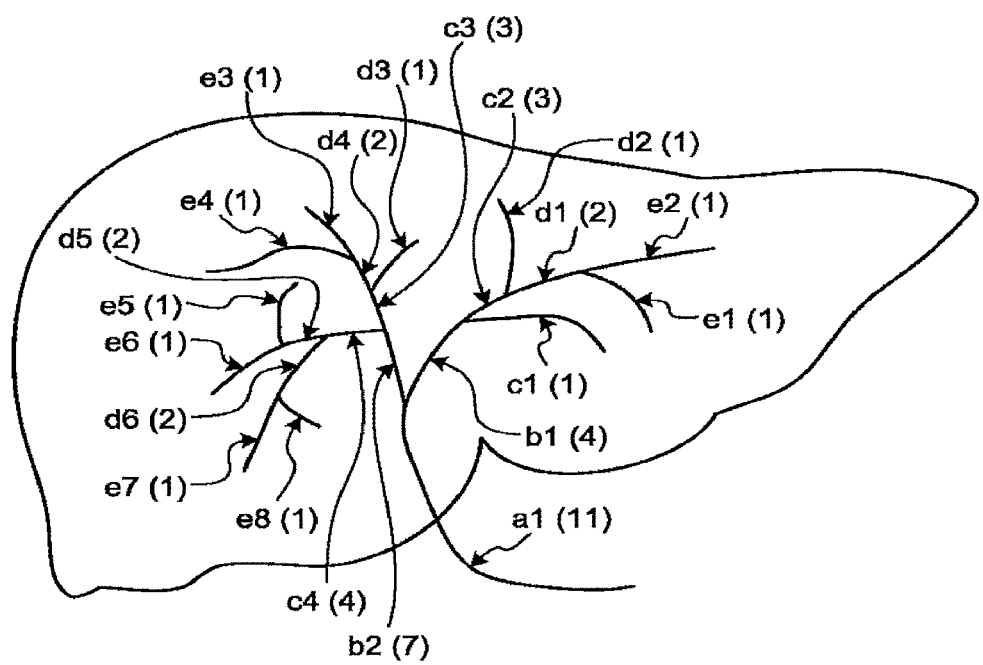

Next, processing when the calculating function 113 calculates the end point is explained using FIG. 8B. A numeral in brackets shown beside a tag of a line segment region in FIG. 8B indicates the end point that is calculated for the line segment region.

As illustrated in FIG. 8B, for example, the calculating function 113 assigns a total value of end points of multiple branch vessels to a branch vessel at a branch source at each point at which branch vessels are unified with a branch vessel at a branch source as going upstream from ends of branch vessels.

First, the calculating function 113 calculates end points sequentially from a line segment region at an end. Specifically, the calculating function 113 calculates the end point "1" for a line segment region that includes an end portion. That is, the calculating function 113 calculate the end point "1" for 11 line segment regions c1, d2, d3, e1, e2, e3, e4, e5, e6, e7, e8 that include an end portion (tip portion).

Next, the calculating function 113 calculates the end point of a line segment region at a branch source of line segment regions having the end point "1", going upstream from the line segment regions of the end point "1". For example, the calculating function 113 calculates an end point for the line segment region d1 that is the branch source of the line segment region e1. The line segment region d1 is a branch vessel that branches off into the line segment region e1 and the line segment region e2. To the line segment region e1 and the line segment region e2, the end point "1" is assigned to each. In this case, the calculating function 113 calculates a total value "2" of the end points of the line segment region e1 and the line segment region e2, as the end point of the line segment region d1. This indicates that the number of end portions (tip portions) that are supplied with blood through the line segment region d1 is "2".

Similarly, going upstream from the line segment region d1 to the line segment region c2, the calculating function 113 calculates the end point "3" (total value of the line segment regions d1 and d3) of the line segment region c2. Furthermore, the calculating function 113 calculates the end point "4" (total value of the line segment regions c1 and c2) of the line segment region b1.

For the other line segment regions also, the calculating function 113 assigns a total value of end points of multiple branch vessels to a branch vessel at a branch source at each point at which branch vessels are unified with a branch vessel at a branch source as going upstream from ends of branch vessels. The calculating function 113 calculates the end point "11" (total value of the line segment regions b1 and b2) of the line segment region a1 finally.

Note that what is explained in FIG. 8A and FIG. 8B is only an example, and it is not limited thereto. For example, although a case in which the evaluation value (the tumor point and the end point) is calculated going upstream from a branch vessel at an end is explained for convenience of explanation, it is not limited thereto. For example, the calculating function 113 can calculate, for each arbitrary line segment region (for example, a ling segment region selected randomly), an end point by counting the number of tip portions supplied with blood through the line segment region.

Moreover, although a case in which the number of tumors or the number of end portions is acquired as an evaluation value as it is has been explained in FIG. 8A and FIG. 8B, embodiments are not limited thereto. For example, it can be a value according to the number of tumors or the number of end portions (for example, a proportional value). Alternatively, the calculating function 113 can calculate the tumor point, for example, by assigning weights according to the size of a tumor that is supplied by each branch vessel. Alternatively, the calculating function 113 can calculate the end point by assigning weights according to at least one of length and thickness of each branch vessel.

At step S107, the calculating function 113 calculates a delivery efficiency of each line segment region. For example, the calculating function 113 calculates a delivery efficiency that expresses the efficiency in delivering a drug to be given from a catheter to each target area based on a branching state and a target connecting state of blood vessels. For example, the calculating function 113 calculates the delivery efficiency of a drug to be given from a catheter by using at least one of the tumor point and the end point.

Figure 9:
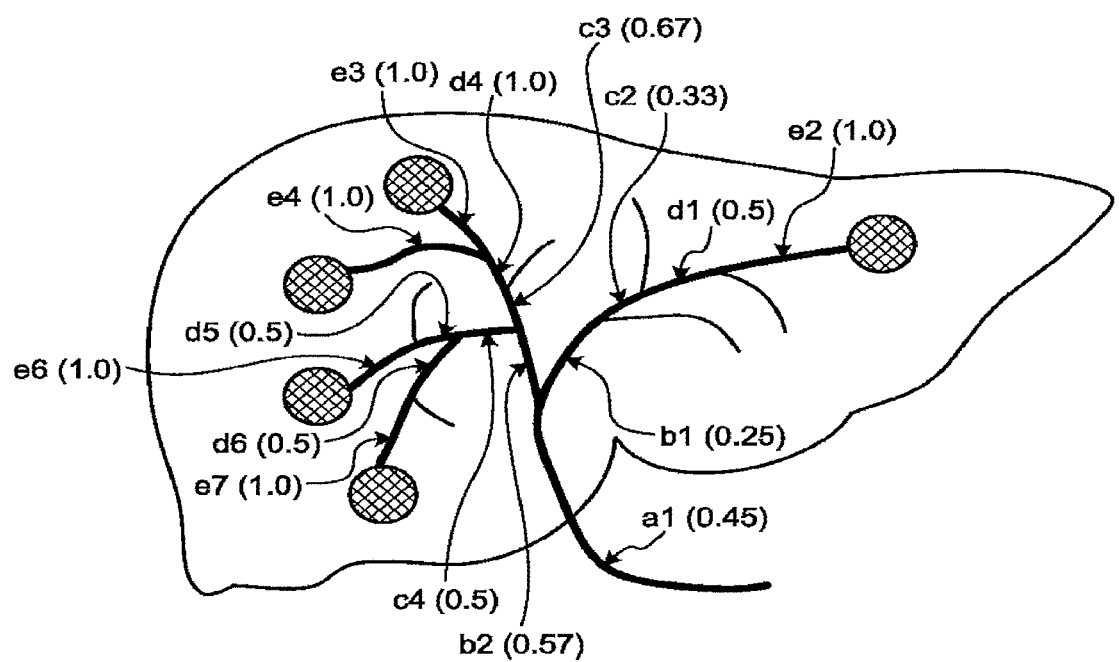
FIG. 9 is a diagram for explaining processing performed by the X-ray diagnostic apparatus according to the first embodiment.

As illustrated in FIG. 9, for example, the calculating function 113 calculates a value that is obtained by dividing the tumor point by the end point as the delivery efficiency. As an example, the tumor point of the line segment region a1 is "5", and the end point is "11". In this case, the calculating function 113 calculates a value "0.45" obtained by dividing "5" by "11" as the delivery efficiency of the line segment region a1.

As described, the calculating function 113 calculates the delivery efficiency by dividing the tumor point by the end point for each of the line segment regions. Note that what is explained in FIG. 9 is only an example, and it is not limited thereto. In other words, the calculating function 113 calculates the delivery efficiency based on a rate of the number of end portions (tumor point) connected to target areas out of the number of end portions (end point) of blood vessel to which blood is supplied from each position of the blood vessels.

At step S108, the calculating function 113 determines a recommended delivery region at which the delivery efficiency is equal to or higher than a threshold. For example, the calculating function 113 accepts specification of the threshold for the delivery efficiency from an operator. The calculating function 113 determines a line segment region having the delivery efficiency equal to or higher than the accepted threshold as the recommended delivery region.

Figure 10:
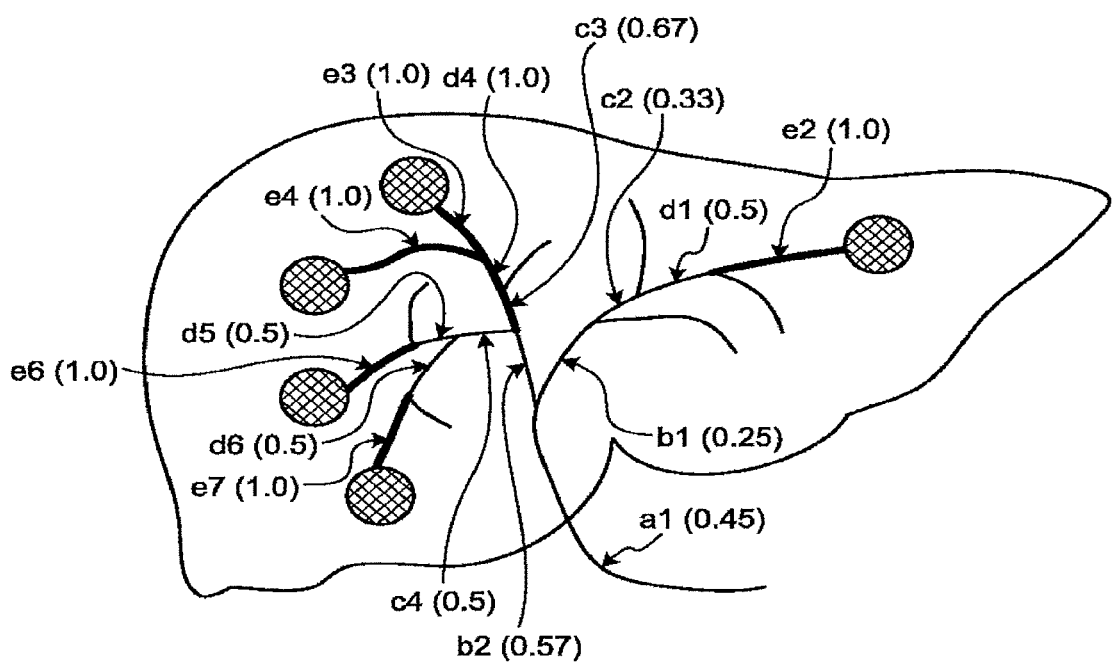
FIG. 10 is a diagram for explaining processing performed by the X-ray diagnostic apparatus according to the first embodiment.

In an example illustrated in FIG. 10, a case in which a threshold of the delivery efficiency "0.67" is specified by an operator is explained. The operator specifies a threshold of the delivery efficiency, for example, considering a type of drug or a condition of the subject P. Line segment regions, the delivery efficiency of which is equal to or higher than the threshold "0.67" are seven line segment regions e2, c3, d4, e3, e4, e6, e7 (thick lines in FIG. 10). In this case, the calculating function 113 determines the seven line segment regions e2, c3, d4, e3, e4, e6, e7 as the recommended delivery regions.

The recommended delivery regions are not limited to be a single region in which multiple line segment regions are continuous, but can include groups of some regions. In the example in FIG. 10, the recommended delivery region includes four groups. Specifically, the recommended delivery region includes a group G1 including the line segment region e2, a group G2 including the four line segment regions c3, d4, e3, e4, a group G3 including the line segment region e6, and a group G4 including the line segment region e7. This indicates that if a drug is given to the groups G1, G3, G4, one tumor each can be necrosed, and if the drug is given to the group G2, two tumors can be necrosed at a time. In other words, the calculating function 113 can perform preferable grouping to necrose multiple tumors efficiently by determining the recommended delivery regions. In FIG. 10, the calculating function 113 classifies branch vessels to which a drug is given to necrose five tumors into four groups.

As described, the calculating function 113 classifies regions of multiple branch vessels, the delivery efficiency of which is equal to or higher than the threshold into one or more groups. Note that what is explained in FIG. 10 is only an example, and it is not limited thereto. For example, the threshold of the delivery efficiency can be set automatically based on a type of drug or a condition of the subject P.

At step S109, the calculating function 113 determines a recommended moving route. For example, the calculating function 113 acquires plural delivery points that are points at which a drug is given to the target areas from a catheter moved inside blood vessels based on a blood vessel structure of blood vessels, and a target connecting state among the target areas and the branch vessels. The calculating function 113 calculates a recommended moving route of a catheter based on the delivery points. For example, the calculating function 113 calculates a recommended moving route based on the delivery efficiency.

For example, the calculating function 113 identifies a branching state of branch vessels that constitute the blood vessel structure of the blood vessels, and calculates a recommended moving route based on the identified branching state and the target connecting state. Specifically, the calculating function 113 calculates a route to move a catheter sequentially from a group closer to a start point of the catheter among groups classified in the recommended delivery region, as a recommended moving route.

Figure 11A:
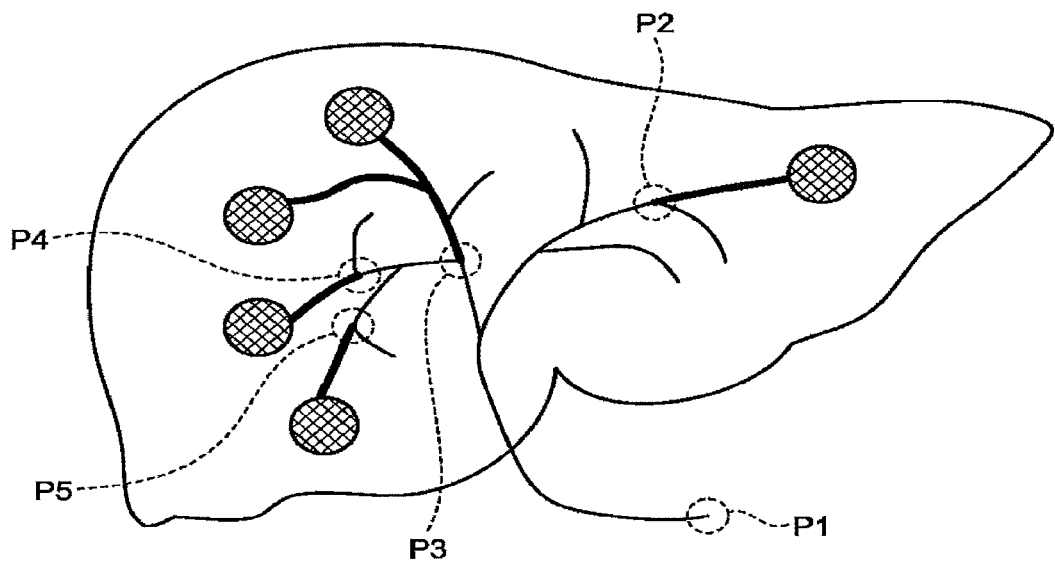
FIG. 11A and FIG. 11B are diagrams for explaining processing performed by the X-ray diagnostic apparatus according to the first embodiment.
Figure 11B:
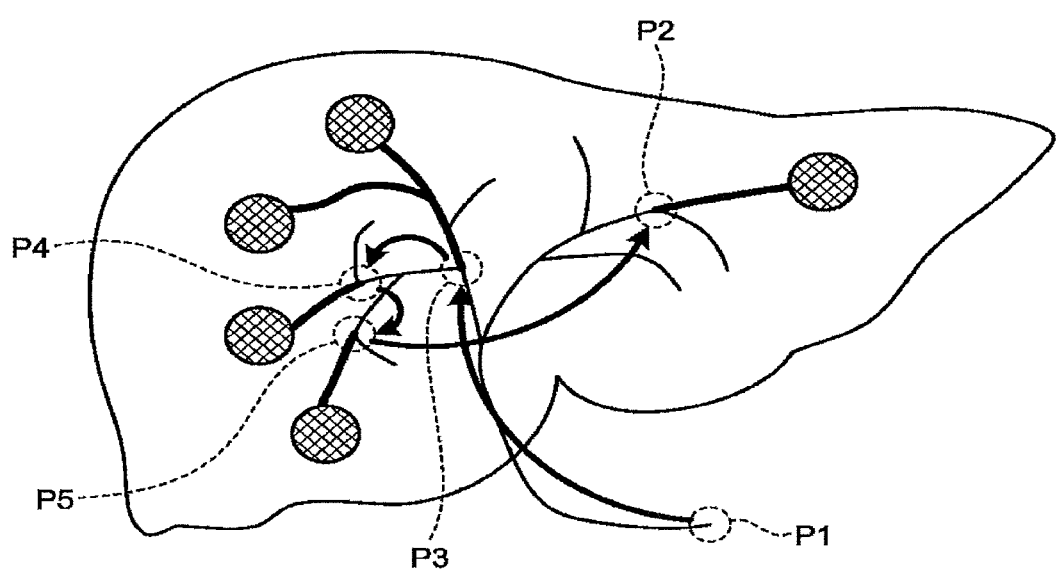

As illustrated in FIG. 11A, the calculating function 113 identifies closest points P2, P3, P4, P5 to a start point P1 in the recommended delivery regions. The point P2 corresponds to a delivery point that is a point at which a drug is given to the tumor region (target area) of the group G1. Moreover, the point P3 corresponds to the delivery point that is a point at which the drug is given to the tumor region of the group G2. The point P4 corresponds to the delivery point that is a point at which the drug is given to the tumor region of the group G3. The point P5 corresponds to the delivery point that is a point at which the drug is given to the tumor region of the group G4. The calculating function 113 calculates a moving route (arrows in FIG. 11B) to move a catheter in order of the start point P1, the point P3, the point P4, the point P5, and the point P2 sequentially, as the recommended moving route as illustrated in FIG. 11B.

As described, the calculating function 113 calculates the recommended moving route. Note that what is explained in FIG. 11A and FIG. 11B is only an example, and it is not limited thereto. For example, it is not necessarily required to insert sequentially from a close point. However, as for a farthest point (point P2 in the example in FIG. 11A and FIG. 11B), it is preferable to give drugs at the last. This is because time to remove the catheter after the procedure is ended can be saved if a far point is treated at the last. In other words, if part points are treated at the last, drug delivery to tumors can be finished in shorter time.

The calculation method of a recommended moving route described above is only an example. For example, the calculating function 113 can calculate the recommended moving route using a moving distance of a catheter or the number of delivery of drugs. In this case, for example, conditions about the moving distance or the number of doses is set manually or automatically. As the conditions, for example, an upper limit or a lower limit of the moving distance or the number of doses is set. The calculating function 113 calculates the recommended moving route such that the delivery efficiency is maximized within a range in which the set conditions are satisfied.

Furthermore, a route can be calculated based on a moving speed of a catheter and time for the procedure. For example, the moving speed is set to either one of, for example, "fast", "normal", and "slow" according to experience of the operator. The time for the procedure is an upper limit of time required for the hepatic artery embolization. In this case, when the procedure is done in the set moving speed, the moving distance is set so as to be finished within the time for the procedure. Furthermore, the recommended moving route is calculated such that the delivery efficiency is maximized within a range satisfying the set moving distance.

At step S110, the output control function 114 outputs the recommended moving route. For example, the output control function 114 causes the display 106 to display the recommended moving route illustrated in FIG. 11B. At this time, the output control function 114 can display a branch vessel (feeding vessel) that supplies blood to a hepatic tumor and other branch vessels in different display mode. Specifically, the output control function 114 displays varying the display modes by thickness of lines, line types (solid line, broken line, and the like), color of lines, and combination of these.

Furthermore, the output control function 114 can display image data that indicates the projection efficiency of the respective line segment regions as illustrated in FIG. 9. In this case, it is preferable that the output control function 114 display the respective line segment regions in colors according to the delivery efficiency. Moreover, the output control function 114 can display regions of branch vessels, the delivery efficiency of which is equal to or higher than a threshold.

Furthermore, the output control function 114 stores information indicating the recommended moving route in storage devices inside and outside the apparatus. For example, the output control function 114 stores the information indicating the recommended moving route in the storage 108. Alternatively, the output control function 114 can transmit the information indicating the recommended moving route to another information processing apparatus that is connected by an in-hospital network.

As described, the X-ray diagnostic apparatus 1 calculates and displays the recommended moving route. Note that the processing procedure explained in FIG. 3 is only an example, and it is not limited thereto. For example, as for the respective processing illustrated in FIG. 3, the order can be changed within a range not causing a contradiction in the processing. For example, the processing of calculating a tip point can be performed at any time as long as it is performed after the processing at step S103 is performed.

Furthermore, although it has been explained with illustration of an outline of a hepatitis in FIG. 4 to FIG. 11B for convenience of explanation, processing of extracting an outline of a hepatitis is not necessary in the processing of calculating the recommended moving route. However, it is preferable that an outline of a hepatitis be displayed on a screen when the recommended moving route is displayed.

As described above, in the X-ray diagnostic apparatus 1 according to the first embodiment, the calculating function 113 calculates a recommended moving route of a catheter moved inside blood vessels in volume data in which blood vessels including multiple branch vessels leading to respective target areas based on a blood vessel structure of the blood vessels and a target connecting state among the respective target areas and the respective branch vessels. Moreover, the output control function 114 outputs the recommended moving route. According to this arrangement, the X-ray diagnostic apparatus 1 can present a recommended moving route of a catheter enabling effective movement among plural target areas. Furthermore, the X-ray diagnostic apparatus 1 can present a feeding vessel enabling to necrose some tumors out of plural tumors at a time.

First Modification of First Embodiment

Figure 12:
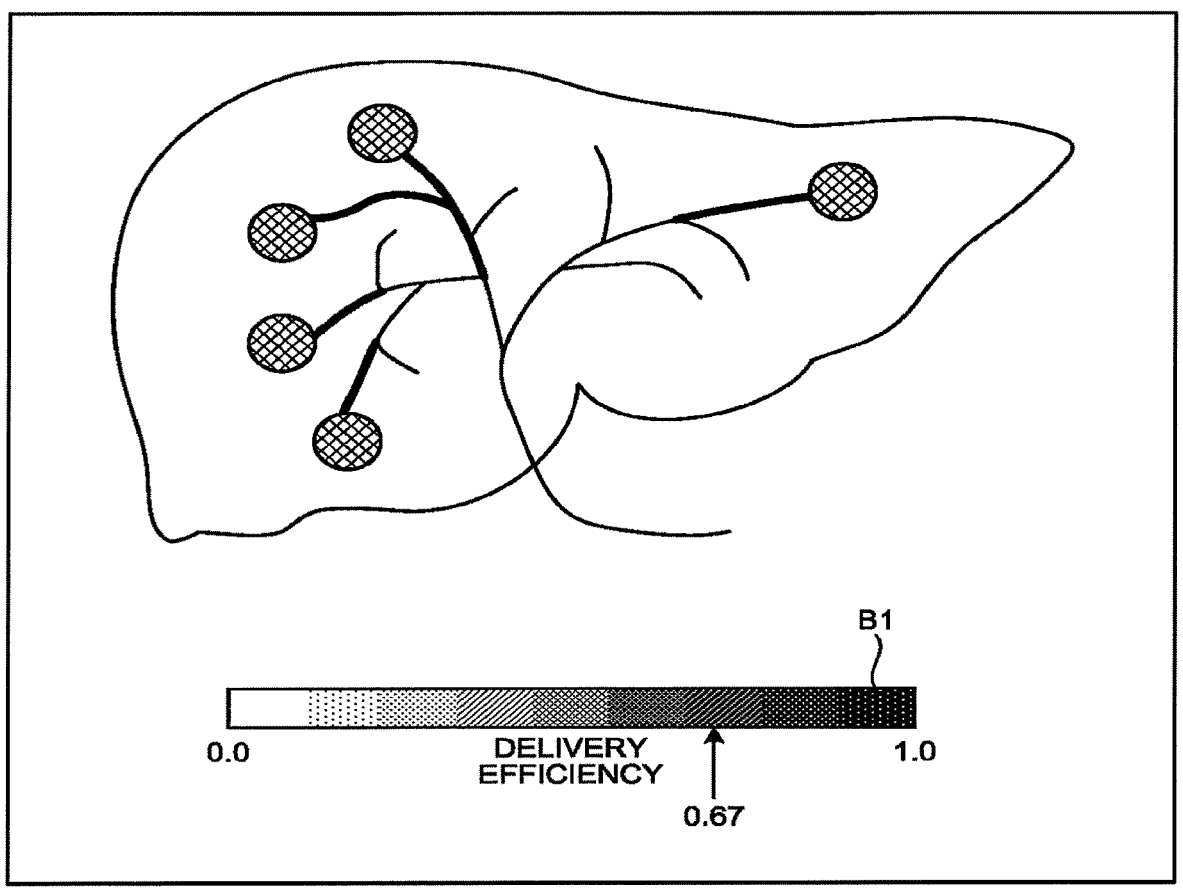
FIG. 12 is a diagram for explaining processing performed by an X-ray diagnostic apparatus according to a first modification of the first embodiment.

For example, the X-ray diagnostic apparatus 1 can further display a slider bar on a screen in which delivery efficiencies of respective line segment regions are displayed. FIG. 12 is a diagram for explaining processing performed by the X-ray diagnostic apparatus 1 according to a first modification of the first embodiment. FIG. 12 illustrates an example of a display screen of the display 106.

For example, the output control function 114 displays a graphical user interface (GUI) to specify a threshold of the delivery efficiency, and displays a branch vessel equal to or higher than the threshold specified through the GUI in a different display mode from other branch vessels.

As illustrated in FIG. 12, for example, an operator specifies an arbitrary value of the delivery efficiency by using a slider bar B1. FIG. 12 illustrates a case in which an operator specifies "0.67". In this case, the output control function 114 displays a line segment region, the delivery efficiency of which is "0.67" or higher in a thick line. Specifically, the output control function 114 displays the line segment regions c3, d4, e2, e3, e4, e6, e7 in thick lines.

Furthermore, when the operator changes the delivery efficiency from "0.67" to "1" in the example in FIG. 12, the output control function 114 displays the line segment region, the delivery efficiency of which is "1" in thick lines. In this case, the output control function 114 displays the line segment regions e2, e3, e4, e6, e7 in thick lines.

Moreover, when the operator changes the delivery efficiency from "0.67" to "0" in the example in FIG. 12, the output control function 114 displays the line segment region, the delivery efficiency of which is "0" or higher in thick lines. In this case, the output control function 114 displays all line segment regions in thick lines.

As described, further displaying the slider bar B1 enables operators to specify an arbitrary delivery efficiency, and to specify an appropriate threshold of the delivery efficiency while changing values as necessary.

Second Modification of First Embodiment

Figure 13:
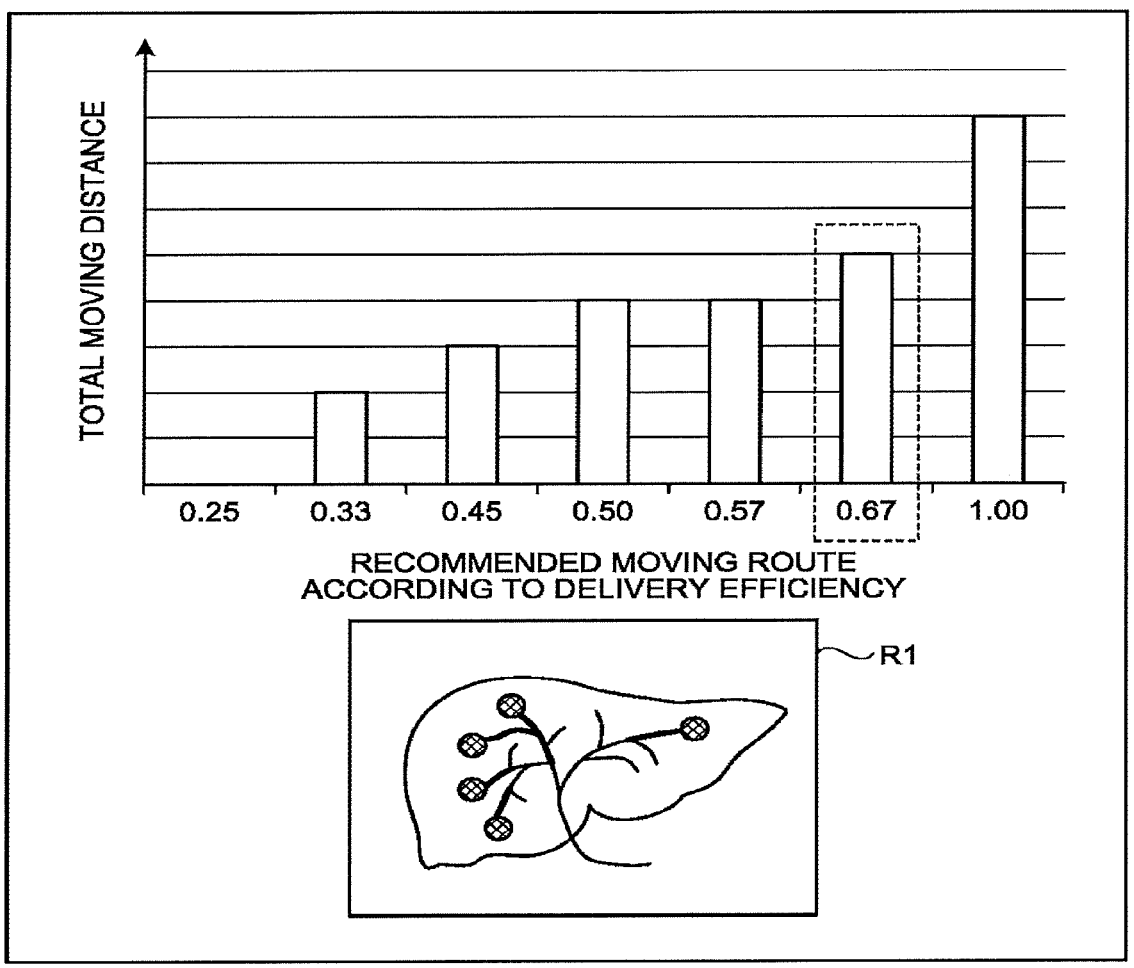
FIG. 13 is a diagram for explaining processing performed by an X-ray diagnostic apparatus according to a second modification of the first embodiment.

Furthermore, for example, the X-ray diagnostic apparatus 1 can present more than one recommended moving route. FIG. 13 is a diagram for explaining processing performed by the X-ray diagnostic apparatus 1 according to a second modification of the first embodiment. FIG. 13 illustrates an example of a display screen of the display 106.

For example, the calculating function 113 calculates plural recommended moving routes for plural delivery efficiencies different from each other. The output control function 114 displays the calculated delivery efficiencies of the respective recommended moving routes and information indicating a relationship between the recommended moving route and a total moving distance.

An upper part of FIG. 13 is a graph expressing the relationship between the recommended moving route according to the delivery efficiency and a total moving distance of each route. For example, for seven delivery efficiencies "0.25", "0.33", "0.45", "0.50", "0.57", "0.67", "1.00", respective recommended moving routes are calculated and displayed. From the graph, it is found that as the delivery efficiency increases, the total moving distance increases. When the operator selects the recommended moving route, the delivery efficiency of which is "0.67", the selected recommended moving route is displayed under the graph as an image R1 (lower part of FIG. 13).

This arrangement makes it easy for an operator to select a recommended moving route according to an arbitrary delivery efficiency. Note that what is explained in FIG. 13 is only an example, and it is not limited thereto. For example, the output control function 114 can further display the number of branch points in each recommended moving route when displaying plural recommended moving routes.

This enables an operator to determine a recommended moving route based on the displayed number of branch points.

Third Modification of First Embodiment

Furthermore, for example, the X-ray diagnostic apparatus 1 can display an index value that is obtained by dividing the delivery efficiency of each recommended moving route by a total moving distance when plural recommended moving routes are displayed.

For example, the output control function 114 displays the index value that is obtained by dividing the delivery efficiency of each recommended moving route by a total moving distance when plural recommended moving routes are displayed. For example, the output control function 114 calculates the index value based on Equation (1) below.

$$\text{Index Value} = \frac{\text{Delivery Efficiency}}{\text{Total Moving Distance}} \quad (1)$$

That is, this index value expresses the delivery efficiency for the total moving distance in each recommended moving route. A recommended moving route with a higher index value has a shorter total moving distance, and can be regarded as a route with high delivery efficiencies. The output control function 114 can output the index value calculated by Equation (1) not only as a numeral value, but also as a graph of the delivery efficiency with respect to the total moving distance.

Fourth Modification of First Embodiment

Furthermore, the X-ray diagnostic apparatus 1 can display a degree of difficulty of each of recommended moving routes when plural recommended moving routes are displayed.

For example, the output control function 114 displays a degree of difficulty of each of recommended moving routes when displaying plural recommended moving routes. For example, the output control function 114 calculates a degree of difficulty based on Equation (2) below.

$$\text{Degree Of Difficulty} = \frac{\text{Distance}}{\text{Volume}} \times \text{Distance} \quad (2)$$

In Equation (2), a distance is a distance of a recommended moving route, and a volume is a volume of each branch Bessel included in the recommended moving route. That is, "distance/volume" expresses a degree of difficulty when inserting a catheter into each branch vessel. By further multiplying this value by a distance, a degree of difficulty according to a total moving distance is expressed. The calculating function 113 can calculate the degree of difficulty based on at least one of thickness of a branch vessel and the number of branch points in each of the recommended moving routes. For example, Equation (2) can be adjusted such that the degree of difficulty decreases as the thickness of a blood vessel increases. Moreover, for example, Equation (2) can be adjusted such that the degree of difficulty increases as the number of branch points increases.

Second Embodiment

In the first embodiment, a case of presenting one or more recommended moving routes has been explained, but a recommended dose of a drug to be given in the presented recommended moving route can also be presented.

For example, the calculating function 113 calculates a recommended dose of a drug to be given in a recommended moving route. Specifically, the calculating function 113 measures a volume of a branch vessel included in the recommended moving route and a volume of a hepatic tumor to which the branch vessel is connected from volume data. The calculating function 113 calculates a recommended dose for the recommended moving route using the measured volumes. The output control function 114 outputs the recommended dose for the recommended moving route.

Figure 14:
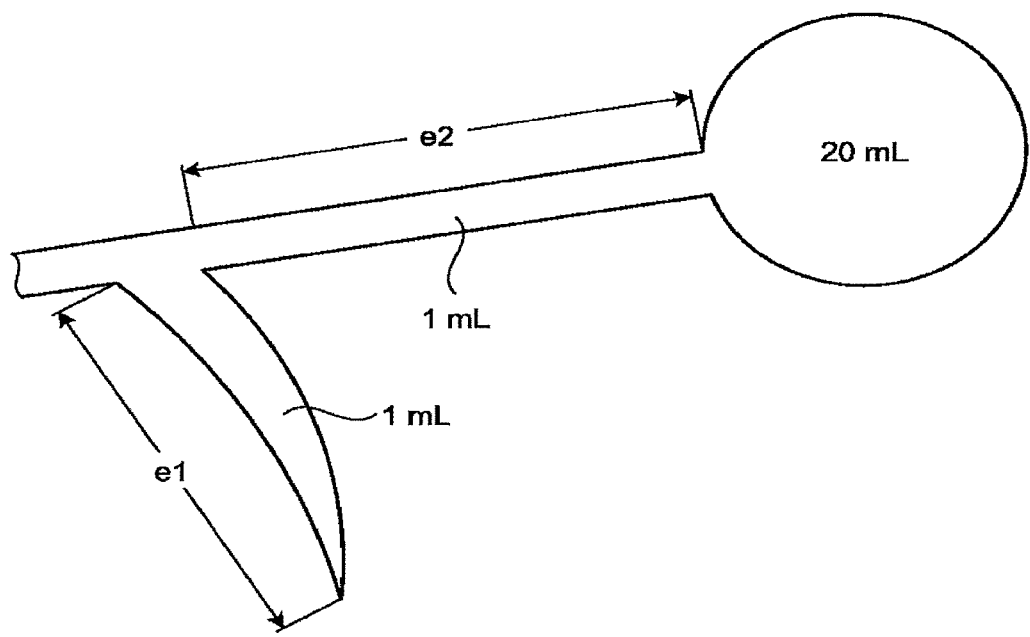
FIG. 14 is a diagram for explaining processing performed by an X-ray diagnostic apparatus according to a second embodiment.

FIG. 14 is a diagram for explaining processing performed by an X-ray diagnostic apparatus 1 according to a second embodiment. FIG. 14 illustrates an enlarged view around the line segment region e1 explained in the first embodiment.

As illustrated in FIG. 14, based on the processing explained in the first embodiment, it is presented that a drug is to be given starting from the point P2 toward a direction of the line segment region e2. In this case, the calculating function 113 calculates a recommended dose to be given at the point P2 further based on a volume of a branch vessel corresponding to the line segment region e2, and a volume of a hepatic tumor to which the line segment region e2 is connected.

For example, the calculating function 113 calculates the volume of the branch vessel corresponding to the line segment region e2, and the volume of the hepatic tumor to which the line segment region e2 is connected from volume data. When the volume of the branch vessel corresponding to the line segment region e2 is "1 milliliter (mL)", and the volume of the hepatic tumor to which the line segment region e2 is connected is "20 mL", the calculating function 113 calculates the total value of those "21 mL" as the recommended dose.

Note that what is explained in FIG. 14 is only an example, and it is not limited thereto. For example, a case in which the total value of the volumes of the branch vessel and the hepatic tumor is regarded as the recommended dose has been explained in FIG. 14, but it is not limited thereto. That is, the calculating function 113 can calculate a value based on volumes of a branch vessel and a hepatic tumor, such as a value proportional to the volumes of the branch vessel and the hepatic tumor, as a recommended dose. Moreover, the calculating function 113 can calculate a recommended dose for each of recommended moving routes by using a volume, a minimum diameter, an average diameter, and the like of a branch vessel included in the recommended moving route.

Third Embodiment

Although a case in which one hepatic tumor is fed by one branch vessel as been explained as an example, not limited thereto, a case in which one hepatic tumor is fed by multiple branch vessels can also be considered in an actual situation. Therefore, in a third embodiment, processing performed when one hepatic tumor is fed by multiple branch vessels is explained.

For example, when multiple branch vessels are connected to one target area, the calculating function 113 calculates a recommended moving route by unifying the branch vessels. For example, the calculating function 113 acquires the tumor point for the branch vessels connected to a common tumor without summing the tumor points when the tumor point of a different branch vessel is calculated.

FIG. 15 is a diagram for explaining processing performed by the X-ray diagnostic apparatus 1 according to a third embodiment. FIG. 15 illustrates a case in which one hepatic tumor T1 is fed by line segment regions f1, f2, f3. A numeral in brackets shown beside a tag of a line segment region in FIG. 15 indicates the tumor point that is calculated for the line segment region. The tumor point is information by which a hepatic tumor the tumor point is based on can be identified. Specifically, "1-T1" in FIG. 15 indicates that the tumor point based on the hepatic tumor T1 is "1".

As illustrated in an upper part of FIG. 15, the calculating function 113 does not sum values based on a common hepatic tumor when calculating the tumor point of the respective line segment regions. For example, the tumor point if the line segment regions f1, f2, f3 is "1-T1", respectively.

When calculating the tumor point, the calculating function 113 handles tumor points as one tumor point without summing them if the tumor points are based on the same hepatic tumor. For example, a line segment region f4 is a branch vessel that branches off into the line segment region f1 and the line segment region f2. In this situation, the tumor point of the line segment region f1 is "1-T1" and the tumor point of the line segment region f2 is also "1-T1". In this case, the calculating function 113 assigns the tumor point "1-T1" to the line segment region f4, not the total value "2" of the tumor points of the line segment region f1 and the line segment region f2.

Furthermore, for example, a line segment region f5 is a branch vessel that branches off into a line segment region f3 and the line segment region f4. In this situation, the tumor point of the line segment region f3 is "1-T1" and the tumor point of the line segment region f4 is also "1-T1". In this case, the calculating function 113 assigns the tumor point "1-T1" to a line segment region f5, not the total value "2" of the tumor points of the line segment region f3 and the line segment region f4.

As described, the calculating function 113 can handle the line segment regions f1, f2, f3, f4, f5 as if to be a single line segment region F1 as illustrated in a lower part of FIG. 15.

Note that a volume of unified line segment regions is to be the total of volumes of the respective line segment regions subjected to unification when using volumes of branch vessels as explained in the second embodiment. For example, a volume of the line segment region F1 is the total value of volumes of the respective line segment regions f1, f2, f3, f4, f5.

Other Embodiments

In addition to the embodiments described above, it can be implemented by various different forms.
Use of Parameters Other than Number of End Portions of Blood Vessels In the embodiments described above, a case in which a delivery efficiency is calculated using the number of end portions of blood vessels has been explained, but embodiments are not limited thereto. For example, the calculating function 113 can calculate a delivery efficiency by using length, area, or volume of a blood vessel region or a tumor region, in addition to the number of end portions of blood vessels.

Figure 16:
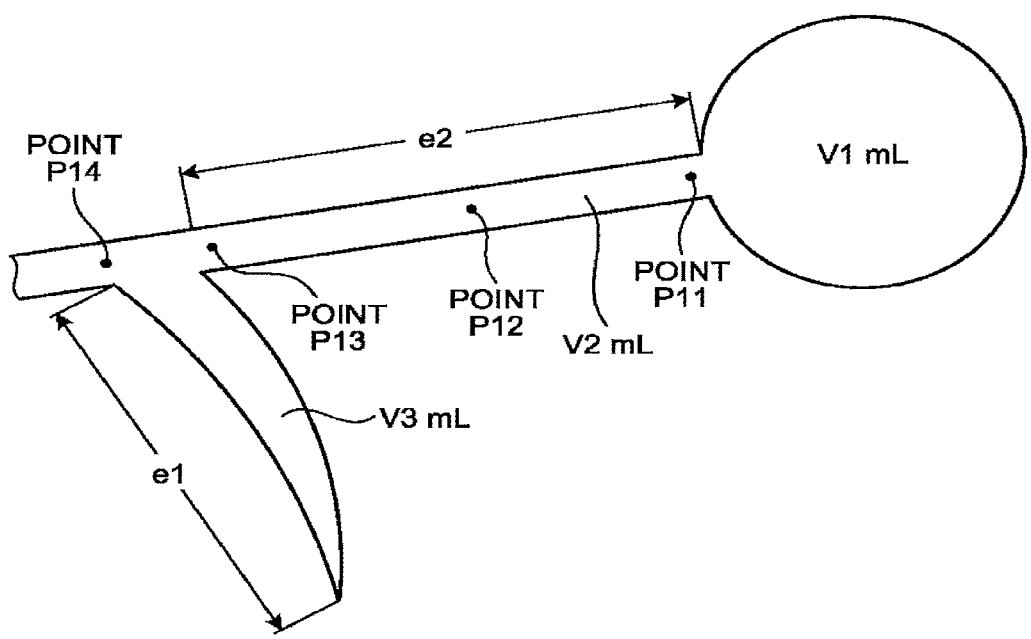
FIG. 16 is a diagram for explaining processing performed by an X-ray diagnostic apparatus according to another embodiment.

FIG. 16 is a diagram for explaining processing performed by an X-ray diagnostic apparatus according to another embodiment. In FIG. 16, a case of calculating a delivery efficiency using volumes is explained. FIG. 16 illustrates a branch vessel that branches off into the line segment regions e1, e2, and a hepatic tumor to which the line segment region e2 is connected. In FIG. 16, the volume of the hepatic tumor is V1 mL, and the volume of the line segment region e2 is V2 mL, and the volume of the line segment region e1 is V1 mL.

As illustrated in FIG. 16, out of tissues to which blood is supplied from respective points of blood vessels, the calculating function 113 calculates a delivery efficiency based on a rate of a target area to which blood is supplied from that point. For example, the calculating function 113 calculates a delivery efficiency for each of four points of points P11 to P14.

The point P11 is a point connecting to the hepatic tumor out of the line segment region e2. Therefore, a tissue to which blood is supplied from the point P11 is the hepatic tumor, and the volume of the hepatic tumor is "V1". Moreover, the volume of the hepatic tumor to which blood is supplied from the point P11 is "V1". That is, the calculating function 113 calculates "V1/V1" as the delivery efficiency at the point P11.

A point P12 is a point corresponding to a middle point of the line segment region e2. Therefore, a volume of a tissue to which blood is supplied from the point P12 correspond to a sum "V1+V2/2" of the volume "V1" of the hepatic tumor and a half the volume "V2/2" of the volume of the line segment region e2. Furthermore, the volume of the hepatic tumor to which blood is supplied from the point P12 is "V1". That is, the calculating function 113 calculates "V1/(V1+V2/2)" as the delivery efficiency at the point P12.

A point P13 is a point closes to the start point of a catheter in the line segment region e2. Therefore, a volume of a tissue to which blood is supplied from the point P13 correspond to a sum "V1+V2" of the volume "V1" of the hepatic tumor and the volume "V2" of the volume of the line segment region e2. Furthermore, the volume of the hepatic tumor to which blood is supplied from the point P13 is "V1". That is, the calculating function 113 calculates "V1/(V1+V2)" as the delivery efficiency at the point P13.

A point P14 is a branch point at which a blood vessel branches off into the line segment regions e1, e2. Therefore, a volume of a tissue to which blood is supplied from the point P14 correspond to a sum "V1+V2+V3" of the volume "V1" of the hepatic tumor and a half the volume "V2/2" of the volume of the line segment region e2, and a volume "V3" of the line segment region e1. Furthermore, the volume of the hepatic tumor to which blood is supplied from the point P14 is "V1". That is, the calculating function 113 calculates "V1/(V1+V2+V3)" as the delivery efficiency at the point P14.

As described, the calculating function 113 calculates a delivery efficiency based on a rate of a volume of a target area to which blood is supplied from respective points out of a volume of a tissue (blood vessel region and target area) to which blood is supplied from respective points of blood vessels.

Although a case in which the delivery efficiency is calculated using volumes has been explained in FIG. 16, embodiments are not limited thereto. For example, the calculating function 113 can calculate the delivery efficiency using length (length of a core line of a blood vessel region, a diameter of a hepatic tumor, or the like), and an area of a tissue (cross-section area of a blood vessel region or a hepatic tumor, or the like) also. That is, as a value expressing a size of a tissue to which blood is supplied from respective points of blood vessels and a size of a target area to which blood is supplied from that point, values of the number of end portions, the length, the area, the volume, or the like can be arbitrarily used. That is, the calculating function 113 calculates a delivery efficiency based on a rate of a target area to which blood is supplied from that point out of tissues to which blood is supplied from respective points of blood vessels.

When a drug infiltrates from a blood vessel or a hepatic tumor, a volume can be calculated considering a depth of infiltration. For example, when a drug infiltrates from a blood vessel for about 5 millimeters (mm) into a periphery, the calculating function 113 cam calculate a volume considering the blood vessel and an infiltration region by calculating a volume with 5 mm added to a radius of the blood vessel. In other words, the rate to calculate a delivery efficiency described above is not limited to the "divided value", but can be a rate subjected various kinds of correction (calculation) to reflect a condition of a patient or a lesion more accurately.

Weight Settings

In the above embodiment, calculation of an index value using weights set in advance by, for example, an experienced doctor is also enabled.

Specifically, the calculating function 113 assigns weights set in advance to respective parameters relating to respective recommended moving route for each of the recommended moving routes, and calculates an index value of each of the recommended moving routes based on the weighted parameters. The output control function 114 displays the index values of the respective recommended moving routes.

For example, the calculating function 113 calculates plural recommended moving routes as illustrated in FIG. 13. The calculating function 113 calculates an index value per recommended moving route. For example, the calculating function 113 appropriately assigns weights to arbitrary parameters, such as a delivery efficiency, a total moving distance, the number of branches, time for procedure, a dose of drug, and a minimum blood vessel radius in each recommended moving route, to calculate an index value. Note that to kinds of parameters and a calculation method used to calculate the index value, a publicly-known method can be applied as appropriate. For example, Equation (1) above is an example of mathematical expression to acquire the index value.

Weights used to calculate the index value are set in advance by an experienced doctor. For example, the doctor sets weights of 0 to 1 to various kinds of parameters. The doctor sets a heavier weight to a more important parameter, and sets a lighter weight to a less important parameter. The calculating function 113 multiplies respective parameters by the weights of the respective parameters set by the doctor. The calculating function 113 then calculates an index value using the parameters subjected to the multiplication. The output control function 114 displays the index values of the respective recommended moving routes along with the respective recommended moving routes.

In the above processing, the calculating function 113 stores the weights of respective parameters set by a doctor in a storage device such as the storage 108. Thus, the calculating function 113 can use the weights of the respective parameters previously set also when index values of respective recommended moving routes are calculated by another doctor (operator) next time or later. The output control function 114 can present a most recommended moving route by comparing index values of respective recommended moving routes.

Medical Image-Processing Apparatus

For example, the respective processing functions of the processing circuitry 110 explained in the above embodiments are also applicable to a medical image-processing apparatus that has a function of processing medical images, such as a work station and a PACS viewer, not limited to the medical diagnostic imaging apparatus.

Figure 17:
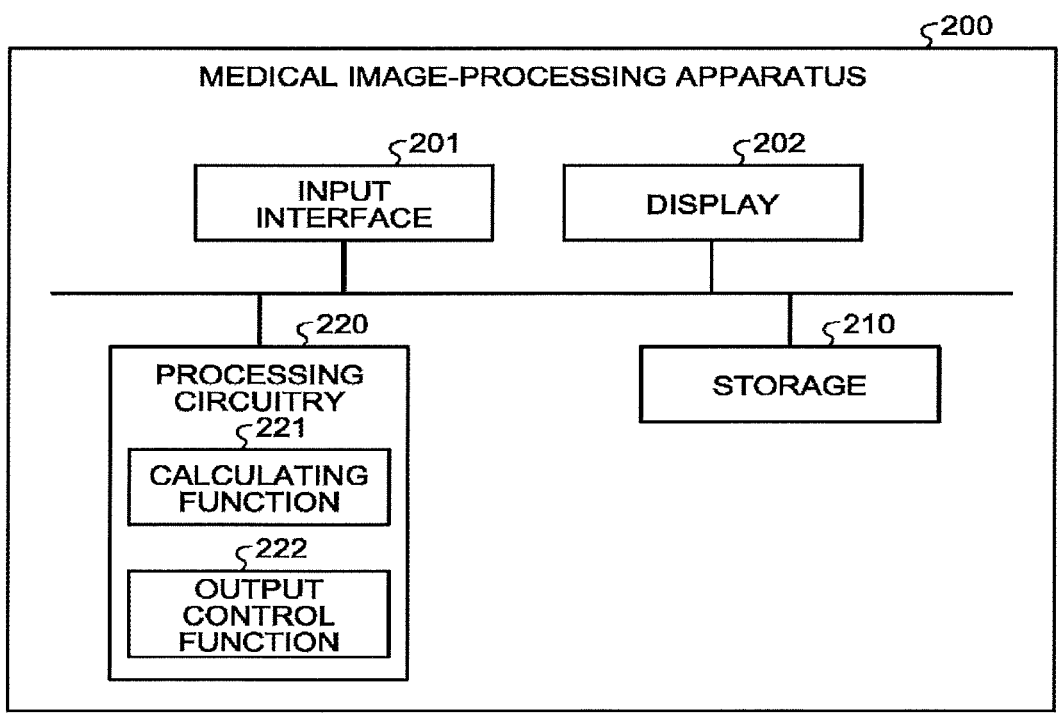
FIG. 17 is a block diagram illustrating an example of a configuration of a medical image-processing apparatus 200 according to another embodiment.

FIG. 17 is a block diagram illustrating an example of a configuration of a medical image-processing apparatus 200 according to another embodiment. The medical image-processing apparatus 200 corresponds to, for example, an information processing apparatus such as a personal computer and a work station, or an operation terminal of a medical diagnostic imaging apparatus such as a console device included in an X-ray diagnostic apparatus.

As illustrated in FIG. 17, the medical image-processing apparatus 200 includes an input interface 201, a display 202, storage 210, and processing circuitry 220. The input interface 201, the display 202, the storage 210, and the processing circuitry 220 are connected to each other to be able to communicate with each other.

The input interface 201 is an input device, such as a mouse, a keyboard, and a touch panel to accept various kinds of instructions and setting requests from an operator. The display 202 is a display device that displays medical images, or displays a GUI for an operator to input various kinds of setting requests by using the input interface 201.

The storage 210 is, for example, a Not AND (NAND) flash memory or a hard disk drive (HDD), and stores various kinds of programs to display medical image data or a GUI, or information used by the programs.

The processing circuitry 220 is an electronic device (processor) that controls entire processing in the medical image-processing apparatus 200. The processing circuitry 220 performs a calculating function 221 and an output control function 222. Respective processing functions performed by the processing circuitry 220 are stored in the storage 210 in a form of a computer-executable program. The processing circuitry 220 reads and executes the respective programs to implement functions corresponding to the respective read programs. The calculating function 221 and the output control function 222 can perform processing similar to that of the calculating function 113 and the output control function 114 illustrated in FIG. 1 basically.

For example, the calculating function 221 functions as the acquiring unit that acquires volume data. For example, the calculating function 221 reads volume data from a storage circuit that stores volume data acquired by a medical diagnostic imaging apparatus. Moreover, the calculating function 221 functions as the extracting unit that extracts a blood vessel structure of blood vessels included in the volume data. Furthermore, the calculating function 221 functions as the setting unit that sets plural target areas in the volume data. Moreover, the calculating function 221 acquires plural delivery points that are points at which a drug is given to target areas from a catheter moved inside blood vessels, and calculates a recommended moving route of the catheter based on the delivery points. Furthermore, the output control function 222 outputs the recommended moving route. According to this arrangement, the medical image-processing apparatus 200 can present a recommended moving route in which a catheter can be moved efficiently among plural target areas.

The respective processing functions of the processing circuitry 110 explained in the above embodiments can also be implemented by software. For example, the respective processing functions of the processing circuitry 110 can be implemented by causing a computer to execute a program in which procedures of the processing explained as to be performed by the respective processing functions of the processing circuitry 110 in the above embodiments are defined. This program (medical image-processing program)

is stored, for example, in a hard disk, a semiconductor memory device, and the like, and is read and executed by a processor such as a CPU and a micro-processing unit (MPU). This program can be recorded on a computer-readable recording medium, such as a compact-disc read-only memory (CD-ROM), a magneto-optical disk (MO), and a digital versatile disc (DVD), to be distributed.

A term "processor" used in the above explanation signifies, for example, a circuit such as a CPU, a graphical processing unit (GPU), an application specific integrated circuit (ASIC), a programmable logic device (for example, a simple programmable logic device (SPLD), and a complex programmable logic device (CPLD)), and a field programmable gate array (FPGA). The processor reads and executes a program installed in a circuit of the processor, and thereby implements a function. Instead of installing the program in a circuit of the processor, the program can be stored in a storage circuit included in a console. In this case, the processor reads and executes the program stored in the storage circuit to implement the function. The respective processors in the present embodiment is not limited to be structured as a single circuit per processor, but can be structured by combining multiple independent processors to form a single processor to implement the functions. Furthermore, more than one component in FIG. 1 can be integrated to a single processor to implement the functions.

Moreover, the respective components of the respective devices illustrated are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, all or a part of the processing explained as to be performed automatically out of the respective processing explained in the above embodiments can be performed manually also, while all or a part of the processing explained as to be performed manually can be performed automatically also by a publicly-known method. In addition, the processing procedures, the control procedures, the specific names, and the information including various kinds of data and parameters indicated in the above document and the drawings can be arbitrarily modified unless otherwise specified.

According to at least one of the embodiments explained above, a recommended moving route of a catheter enabling efficient movement among plural target areas can be presented.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image-processing apparatus comprising processing circuitry configured to:

acquire volume data in which a blood vessel including a plurality of branch vessels leading to a plurality of target areas, respectively, is imaged, extract a blood vessel structure of the blood vessel included in the volume data, set a plurality of the target areas in the volume data, identify a plurality of delivery points that are points at which a drug is given to the target areas from a catheter moved inside the blood vessel based on the blood vessel structure of the blood vessel and a positional relationship between the respective target areas and the respective branch vessels in the volume data, identify a branching state of the branch vessels that constitute the blood vessel structure of the blood vessel, calculate a recommended moving route of the catheter based on the plurality of delivery points, the identified branching state, and a target connecting state among the respective target areas and the respective branching vessels, and output the recommended moving route.

2. The medical image-processing apparatus according to claim 1, wherein the processing circuitry calculates a delivery efficiency that expresses an efficiency in delivering a drug to be given from the catheter to the respective target areas based on a rate of the target areas out of tissues to which blood is supplied from respective points of the blood vessel, the target areas to which blood is supplied from the points.

3. The medical image-processing apparatus according to claim 2, wherein the processing circuitry calculates, as the rate, a rate of number of end portions that lead to the target areas out of number of end portions of a blood vessel to which blood is supplied from respective points of the blood vessel, or a rate of length of the target areas out of length of a blood vessel region and the target areas to which blood is supplied from respective points of the blood vessel.

4. The medical image-processing apparatus according to claim 2, wherein the processing circuitry calculates, as the rate, a rate of an area of the target areas out of an area of a blood vessel region and the target areas to which blood is supplied from respective points of the blood vessel, or a rate of a volume of the target areas out of a volume of the blood vessel region and the target areas.

5. The medical image-processing apparatus according to claim 1, wherein the processing circuitry calculates a delivery efficiency that expresses an efficiency in delivering a drug to be given from the catheter to the respective target areas based on the branching state and the target connecting state, and calculates the recommended moving route based on the calculated delivery efficiency.

6. The medical image-processing apparatus according to claim 5, wherein the processing circuitry classifies regions of the branch vessels, the delivery efficiency of which is equal to or higher than a threshold into at least one group, and calculates a route in which the catheter is moved sequentially from a group that is positioned close to a starting point of the catheter out of the groups obtained by classification, as the recommended moving route.

7. The medical image-processing apparatus according to claim 5, wherein the processing circuitry calculates a plurality of the recommended moving routes for each of the delivery efficiencies different from each other, and the processing circuitry displays information indicating a relationship between the delivery efficiency of each of the recommended moving routes and a total moving distance of the recommended moving routes.

8. The medical image-processing apparatus according to claim 7, wherein the processing circuitry displays an index value that is obtained by dividing the delivery efficiency by a total moving distance of the respective recommended moving routes when displaying the recommended moving routes.

9. The medical image-processing apparatus according to claim 7, wherein the processing circuitry when displaying the recommended moving routes, calculates a degree of difficulty of the respective recommended moving routes based on at least one of a thickness of a branch vessel and number of branch points in each of the recommended moving routes, displays the degree of difficulty of the respective recommended moving routes.

10. The medical image-processing apparatus according to claim 7, wherein the processing circuitry displays number of branch points in the respective recommended moving routes when displaying the recommended moving routes.

11. The medical image-processing apparatus according to claim 5, wherein the processing circuitry calculates the delivery efficiency based on at least one of a first evaluation value according to number of tumors reached through the respective branch vessels, and a second evaluation value according to number of end portions reached through the respective branch vessels.

12. The medical image-processing apparatus according to claim 11, wherein the processing circuitry calculates the first evaluation value by assigning weights according to a size of a tumor reached through the respective branch vessels.

13. The medical image-processing apparatus according to claim 1, wherein the processing circuitry calculates the recommended moving route using any one of a moving distance of the catheter and number of doses of a drug.

14. The medical image-processing apparatus according to claim 1, wherein the processing circuitry calculates the recommended moving route based on a moving speed of the catheter and time for procedure.

15. The medical image-processing apparatus according to claim 1, wherein the processing circuitry calculates a recommended dose of a drug to be given in the recommended moving route, and the processing circuitry outputs the recommended dose in the recommended moving routes.

16. The medical image-processing apparatus according to claim 1, wherein when a plurality of the branch vessels are connected to the one target area, the processing circuitry unifies the branch vessels to calculate the recommended moving route.

17. A medical diagnostic-imaging apparatus comprising processing circuitry configured to:

acquire volume data in which a blood vessel including a plurality of branch vessels leading to a plurality of target areas, respectively, is imaged, extract a blood vessel structure of the blood vessel included in the volume data, set a plurality of the target areas in the volume data, identify a plurality of delivery points that are points at which a drug is given to the target areas from a catheter moved inside the blood vessel based on the blood vessel structure of the blood vessel and a positional relationship between the respective target areas and the respective branch vessels in the volume data, identify a branching state of the branch vessels that constitute the blood vessel structure of the blood vessel, calculate a recommended moving route of the catheter based on the plurality of delivery points, the identified branching state, and a target connecting state among the respective target areas and the respective branching vessels, and output the recommended moving route.

18. A medical image-processing method comprising:

acquiring volume data in which a blood vessel including a plurality of branch vessels leading to a plurality of target areas, respectively, is imaged;

extracting a blood vessel structure of the blood vessel included in the volume data;

setting a plurality of the target areas in the volume data;

identifying a plurality of delivery points that are points at which a drug is given to the target areas from a catheter moved inside the blood vessel based on the blood vessel structure of the blood vessel and a positional relationship between the respective target areas and the respective branch vessels in the volume data;

identifying a branching state of the branch vessels that constitute the blood vessel structure of the blood vessel, calculating a recommended moving route of the catheter based on the plurality of delivery points, the identified branching state, and a target connecting state among the respective target areas and the respective branching vessels, and outputting the recommended moving route.

19. A medical image-processing apparatus comprising processing circuitry configured to:

acquire volume data in which a blood vessel including a plurality of branch vessels leading to a plurality of target areas, respectively, is imaged, extract a blood vessel structure of the blood vessel included in the volume data, set a plurality of the target areas in the volume data, identify a plurality of delivery points that are points at which a drug is given to the target areas from a catheter moved inside the blood vessel based on the blood vessel structure of the blood vessel and a positional relationship between the respective target areas and the respective branch vessels in the volume data, calculate a recommended moving route of the catheter based on the plurality of delivery points, a moving speed of the catheter, and time for procedure, and output the recommended moving route.

20. A medical image-processing apparatus comprising processing circuitry configured to:

acquire volume data in which a blood vessel including a plurality of branch vessels leading to a plurality of target areas, respectively, is imaged, extract a blood vessel structure of the blood vessel included in the volume data, set a plurality of the target areas in the volume data, identify a plurality of delivery points that are points at which a drug is given to the target areas from a catheter moved inside the blood vessel based on the blood vessel structure of the blood vessel and a positional relationship between the respective target areas and the respective branch vessels in the volume data, unify a plurality of the branch vessels when the plurality of the branch vessels are connected to the one target area, calculate a recommended moving route of the catheter based on the plurality of delivery points and the unified the plurality of the branch vessels, and output the recommended moving route.

\* \* \* \* \*